United States Patent
Shia et al.

(10) Patent No.: US 7,834,046 B2
(45) Date of Patent: Nov. 16, 2010

(54) THIOPHENE COMPOUNDS

(75) Inventors: Kak-shan Shia, Taipei (TW);
Chia-Liang Tai, Hsinchu (TW);
Jyh-hsiung Liao, Hsinchu (TW);
Ming-shiu Hung, Taoyuan (TW);
Yu-Sheng Chao, Warren, NJ (US)

(73) Assignee: National Health Research Institutes, Miaoli County (TW)

( * ) Notice: Subject to any disclaimer, the term of this patent is extended or adjusted under 35 U.S.C. 154(b) by 315 days.

(21) Appl. No.: 11/866,263

(22) Filed: Oct. 2, 2007

(65) Prior Publication Data

US 2008/0090810 A1    Apr. 17, 2008
US 2009/0029969 A2    Jan. 29, 2009

Related U.S. Application Data

(60) Provisional application No. 60/848,761, filed on Oct. 2, 2006.

(51) Int. Cl.
*C07D 409/14* (2006.01)
*C07D 409/06* (2006.01)
*C07D 409/04* (2006.01)
*A61K 31/454* (2006.01)
*A61K 31/55* (2006.01)
*A61K 31/4155* (2006.01)

(52) U.S. Cl. .................. 514/406; 514/217.09; 514/326; 540/603; 546/211; 548/365.7

(58) Field of Classification Search ................. 514/406, 514/217.09, 326; 540/603; 546/211; 548/365.7
See application file for complete search history.

(56) References Cited

U.S. PATENT DOCUMENTS

| | | | |
|---|---|---|---|
| 5,624,941 | A | 4/1997 | Barth et al. |
| 6,620,804 | B2 | 9/2003 | Chang et al. |
| 6,958,339 | B2 * | 10/2005 | Kubota et al. .......... 514/255.05 |
| 2001/0011090 | A1 * | 8/2001 | Kubota et al. ............ 514/230.5 |
| 2005/0261281 | A1 | 11/2005 | Lazzari et al. |
| 2008/0021031 | A1 | 1/2008 | Shia et al. |

FOREIGN PATENT DOCUMENTS

| CN | 1709889 A | * 12/2005 |
|---|---|---|
| EP | 1623741 | 2/2006 |
| JP | 2053787 | 2/1990 |
| WO | WO 2007002559 A1 * | 1/2007 |

OTHER PUBLICATIONS

Morimoto et al., caplus an 1970:456092, (1970).
Clark et al., "Decreased Incidence of Prostate Cancer with Selenium Supplementation: Results of a Double-Blind Cancer Prevention Trial," *British Journal of Urology*, 81:730-734 (1998).
Clark et al., "Effects of Selenium Supplementation for Cancer Prevention in Patients with Carcinoma of the Skin," JAMA, 276:1957-1963 (1996).
Diwadkar-Navsariwala et al., "Selenoprotein Deficiency Accelerates Prostate Carcingenesis in a Transgenic Model," *PNAS*, 103(21):8179-8184 (2006).
Database CAS Online on STN, Chem. Abst., Accession No. 2005:1242633, US 20050261281 A1 (Lazzari et al.) Nov. 24, 2005.
Finar, "Preparation and Properties of Some Bipyrazolyls," Journal of the Chemical Society, pp. 12288, (1956).
Tseng et al., "Bioisosteric Replacement of the Pyrazile 5-Aryl Moiety of N-(Piperidin-1-yl)-5-(4-chlorophenyl)-1-(2,4-dichlorophenyl)-4-methyl-1H-pyrazole-3-caroxamide (SR141716A). A Novel Series of Alkynylthiophenes as Potent and Selective Cannabinoid-1 Receptor Antagonists," J. Med. Chem., 51:5397-5412 (2008).
Obata et al., caplus an 1994:700884.

* cited by examiner

*Primary Examiner*—Rebecca L Anderson
*Assistant Examiner*—Matthew P Coughlin
(74) *Attorney, Agent, or Firm*—Occhiuti Rohlicek & Tsao LLP

(57) ABSTRACT

This invention relates to thiophene compounds of formula (I) shown below:

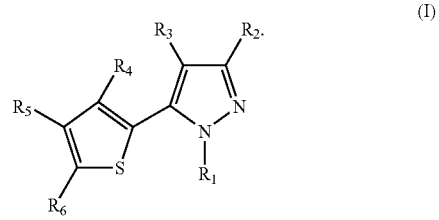

Each variable in formula (I) is defined in the specification. These compounds can be used to treat cannabinoid-receptor mediated disorders.

8 Claims, No Drawings

THIOPHENE COMPOUNDS

CROSS-REFERENCE TO RELATED APPLICATIONS

This application claims the benefit of U.S. Provisional Application No. 60/848,761, filed Oct. 2, 2006. The contents of the foregoing application are hereby incorporated by reference in its entirety.

BACKGROUND

Cannabinoids isolated from *Cannabis sativa* have been recognized for centuries as therapeutic agents. For example, they have been utilized in treating analgesia, muscle relaxation, appetite stimulation, and anti-convulsion. Recent studies also indicate their potential therapeutic effects in treating cancer and alleviating the symptoms of chronic inflammatory diseases, such as rheumatism and multiple sclerosis.

The actions of cannabinoids are mediated by at least two types of the cannabinoid receptors, CB1 and CB2 receptors, both of which belong to the G-protein-coupled receptor (GPCR) superfamily. CB1 receptor is predominantly expressed in brain to mediate inhibition of transmitter release and CB2 receptor is primarily expressed in immune cells to modulate immune response. See Matsuda et al., Nature (1990) 346:561 and Munro et al., Nature (1993) 365:61.

Compared to other GPCRs, CB1 receptor is typically expressed at higher levels. In the central nervous system, it is highly expressed in cerebral cortex, hippocampus, basal ganglia, and cerebellum, but has relatively low levels in hypothalamus and spinal cord. See, e.g., Howlett et al., Pharmacol Rev (2002) 54:161. Its functions affect many neurological and psychological phenomena, such as mood, appetite, emesis control, memory, spatial coordination muscle tone, and analgesia. See, e.g., Goutopoulos et al., Pharmacol Ther (2002) 95:103. Other than the central nervous system, it is also present in several peripheral organs, such as gut, heart, lung, uterus, ovary, testis, and tonsils. See, e.g., Galiègue et al., Eur J Biochem (1995) 232:54.

CB2 receptor is 44% identical to CB1 receptor with a 68% identity in the trans-membrane regions. See Munro et al., Nature (1993) 365:61. Compared to CB1 receptor, CB2 receptor has a more limited distribution with high expression in spleen and tonsils, and low expression in lung, uterus, pancreas, bone marrow, and thymus. Among immune cells, B cells express CB2 receptor at the highest level, followed in order by natural killer cells, monocytes, polymorphonuclear neutrophils, and T lymphocytes. See Galiègue et al., Eur J Biochem (1995) 232:54. Activation of CB2 receptor has been shown to have analgesic effects in inflammatory models involved in neurodegeneration diseases (such as Alzheimer's disease), and play a role in the maintenance of bone density and progression of atherosclerotic lesions. See, e.g., Malan et al., Pain (2001) 93:239; Benito et al., J Neurosci (2003) 23:11136; Ibrahim et al., Proc Natl Acad Sci USA (2003) 100:10529; Idris et al., Nat Med (2005) 11:774; and Steffens et al., Nature (2005) 434:782.

SUMMARY

This invention is based on the discovery that certain thiophene compounds are effective in treating cannabinoid-receptor mediated disorders.

In one aspect, this invention features thiophene compounds of formula (I):

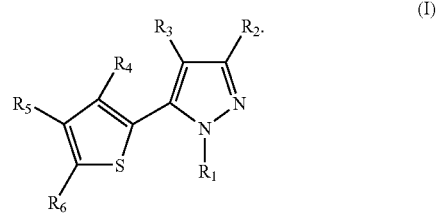

In this formula, $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; $R_2$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $COOR_a$, $OC(O)R_a$, $C(O)R_a$, $C(O)NR_aR_b$, or $NR_aR_b$, in which each of $R_a$ and $R_b$, independently, is H, $C_1$-$C_{10}$ alkyl, $C_3$-$C_{20}$ cycloalkyl, $C_1$-$C_{20}$ heterocycloalkyl, aryl, or heteroaryl; each of $R_3$, $R_4$, and $R_5$, independently, is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or $R_5$, together with $R_6$ and the carbon atoms to which they are attached, is $C_3$-$C_{20}$ cycloalkenyl or $C_3$-$C_{20}$ heterocycloalkenyl; and $R_6$ is $C_2$-$C_{10}$ alkenyl or $C_2$-$C_{10}$ alkynyl; or $R_6$, together with $R_5$ and the carbon atoms to which they are attached, is $C_3$-$C_{20}$ cycloalkenyl or $C_3$-$C_{20}$ heterocycloalkenyl.

Referring to formula (I), some of the thiophene compounds described above have one or more of the following features: $R_1$ is aryl substituted with halo (e.g., 2,4-dichlorophenyl); $R_6$ is alkenyl unsubstituted or substituted with cycloalkyl (e.g., penten-1-yl and 2-cyclohexylethen-1-yl), or alkynyl unsubstituted or substituted with alkoxy, amino, cycloalkyl, heterocycloalkyl, aryl, or heteroaryl (e.g., 2-cyclopentylethyn-1-yl, 2-cyclohexylethyn-1-yl, 2-cyclopropylethyn-1-yl, pent-1-ynyl, hex-1-ynyl, 3-isopropoxy-prop-1-ynyl, 3-dimethylamino-prop-1-ynyl, pyrrolidin-1yl-propyn-1yl, and phenylethyn-1-yl); and $R_2$ is $C(O)R_a$ (in which $R_a$ can be piperidinyl or pyrrolidinyl) or $C(O)NR_aR_b$ (in which each of $R_a$ and $R_b$, independently, can be H, cyclohexyl, piperidinyl, or octahydrocyclopentapyrrolyl).

The term "alkyl" refers to a saturated, linear or branched hydrocarbon moiety, such as —$CH_3$ or —$CH(CH_3)_2$. The term "alkenyl" refers to a linear or branched hydrocarbon moiety that contains at least one double bond, such as —CH=CH—$CH_3$. The term "alkynyl" refers to a linear or branched hydrocarbon moiety that contains at least one triple bond, such as —C≡C—$CH_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In another aspect, this invention features thiophene compounds of formula (I) in which $R_1$ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; $R_2$ is $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $OC(O)R_a$, $NR_aR_b$, or $C_1$-$C_{10}$ alkyl substituted with $NR_a$—C(O)—$R_b$, $NR_a$—C(S)—$R_b$, $NR_a$—C(O)—$NR_bR_c$, $NR_a$—C(S)—$NR_bR_c$, or $NR_a$—C(=N—CN)—$NR_bR_c$, in which each of $R_a$, $R_b$, and $R_c$, independently, is H, $C_1$-$C_{10}$ alkyl, $C_3$-$C_{20}$ cycloalkyl, $C_1$-$C_{20}$ heterocycloalkyl, aryl, or heteroaryl; and each of $R_3$, $R_4$, $R_5$, and $R_6$, independently, is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or $R_5$ and $R_6$, together with the carbon atoms to which they are attached, is $C_3$-$C_{20}$ cycloalkenyl or $C_3$-$C_{20}$ heterocycloalkenyl.

Some of the just-described thiophene compounds have one or more of the following features: $R_1$ is aryl substituted with halo (e.g., 2,4-dichlorophenyl); $R_6$ is chloro or penten-1-yl; and $R_2$ is methyl substituted with $NR_a$—C(O)—$R_b$, $NR_a$—C(O)$NR_bR_c$, or $NR_a$—C(S)—$NR_bR_c$, in which $R_a$ is H, $R_c$ is H, and $R_b$ is cyclopropyl, cyclobutyl, cyclopentyl, cyclohexyl, cycloheptyl, pyridyl, phenyl optionally substituted with halo or $C_1$-$C_{10}$ alkyl, or $C_1$-$C_{10}$ alkyl optionally substituted with aryl or heteroaryl.

In still another aspect, this invention features a method for treating a cannabinoid-receptor mediated disorder. The method includes administering to a subject in need thereof an effective amount of one or more thiophene compounds of formula (I) shown above. Examples of cannabinoid-receptor mediated disorders include liver fibrosis, hair loss, obesity, metabolic syndrome (e.g., syndrome X), hyperlipidemia, type II diabetes, atherosclerosis, substance addiction (e.g., alcohol addiction or nicotine addiction), depression, motivational deficiency syndrome, learning or memory dysfunction, analgesia, haemorrhagic shock, ischemia, liver cirrhosis, neuropathic pain, antiemesis, high intraocular pressure, bronchodilation, osteoporosis, cancer (e.g., prostate cancer, lung cancer, breast cancer, or head and neck cancer), a neurodegenerative disease (e.g., Alzheimer's disease or Parkinson's disease), or an inflammatory disease.

The term "treating" or "treatment" refers to administering one or more thiophene compounds to a subject, who has an above-described disorder, a symptom of such a disorder, or a predisposition toward such a disorder, with the purpose to confer a therapeutic effect, e.g., to cure, relieve, alter, affect, ameliorate, or prevent the above-described disorder, the symptom of it, or the predisposition toward it.

In addition, this invention encompasses a pharmaceutical composition that contains an effective amount of at least one of the above-mentioned thiophene compounds and a pharmaceutically acceptable carrier.

The thiophene compounds described above include the compounds themselves, as well as their salts, prodrugs, and solvates, if applicable. A salt, for example, can be formed between an anion and a positively charged group (e.g., amino) on a thiophene compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a thiophene compound. Suitable cations include sodium ion, potassium ion, magnesium ion, calcium ion, and an ammonium cation such as tetramethylammonium ion. The thiophene compounds also include those salts containing quaternary nitrogen atoms. Examples of prodrugs include esters and other pharmaceutically acceptable derivatives, which, upon administration to a subject, are capable of providing active thiophene compounds. A solvate refers to a complex formed between an active thiophene compound and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the thiophene compounds described above for use in treating an above-described disorder, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are 38 exemplary compounds of this invention:

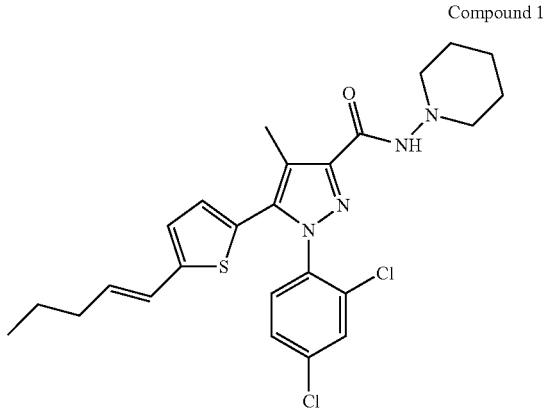

Compound 1

-continued
Compound 2
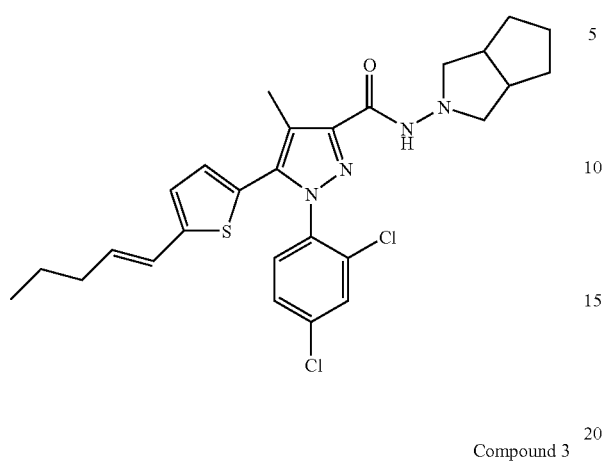
Compound 3
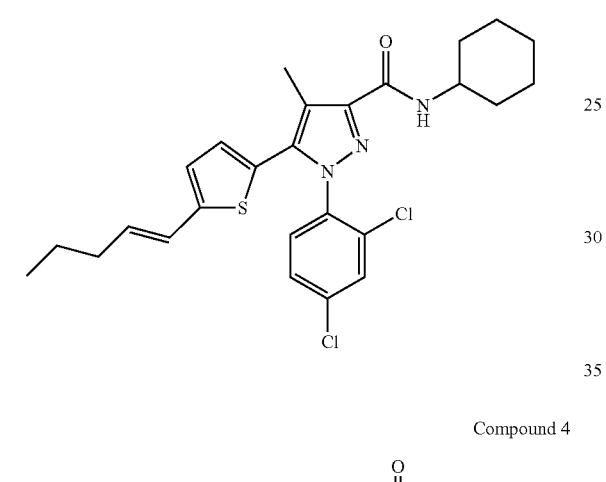
Compound 4
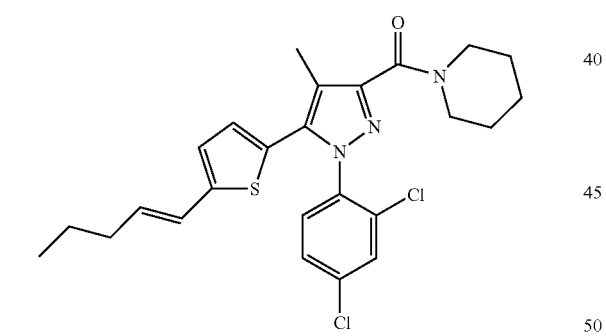
Compound 5
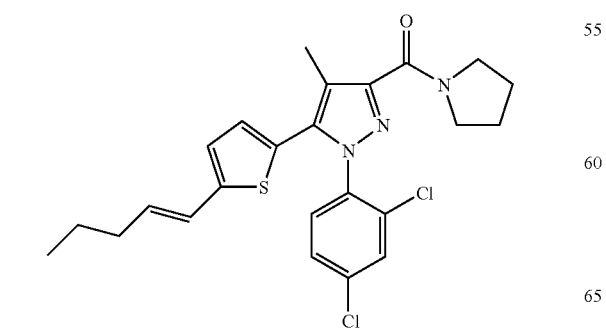
-continued
Compound 6
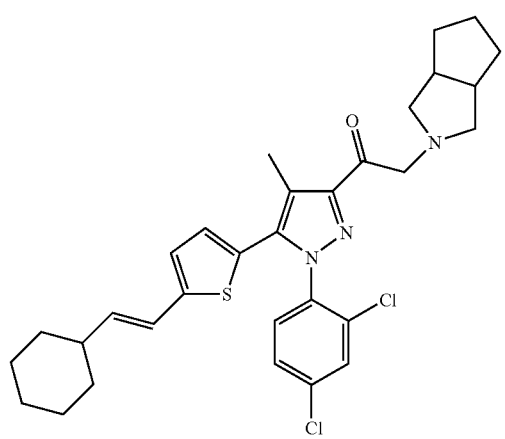
Compound 7
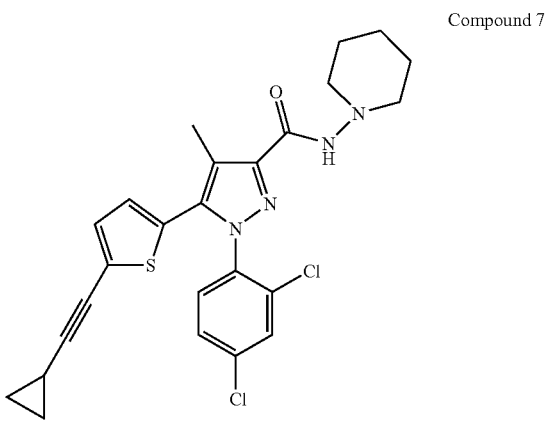
Compound 8
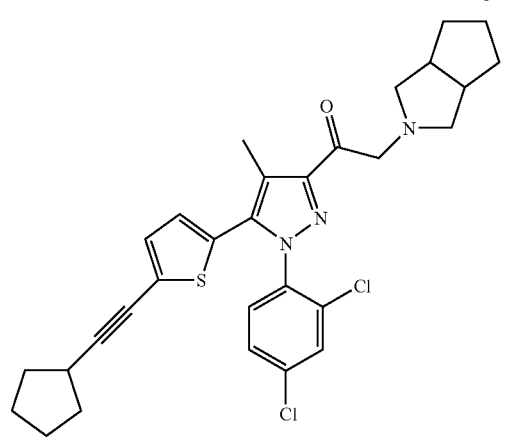

-continued
Compound 9
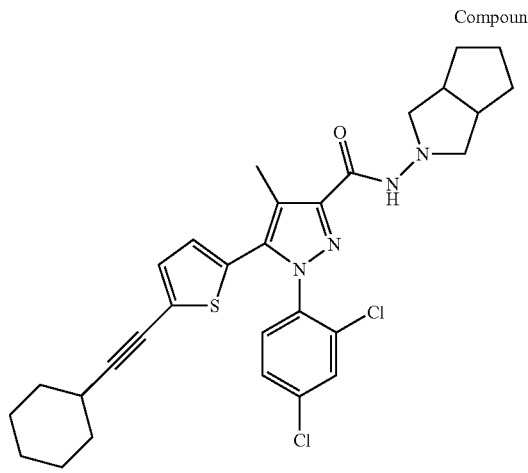
Compound 10
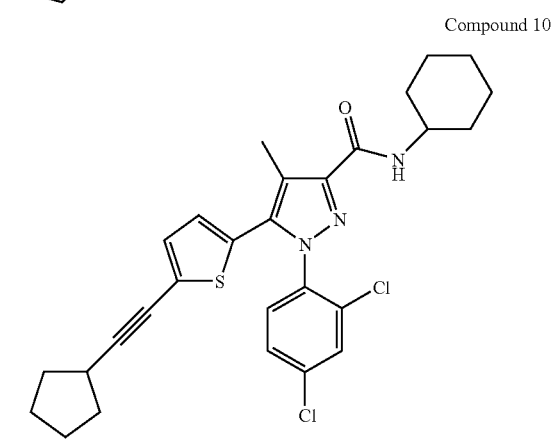
Compound 11
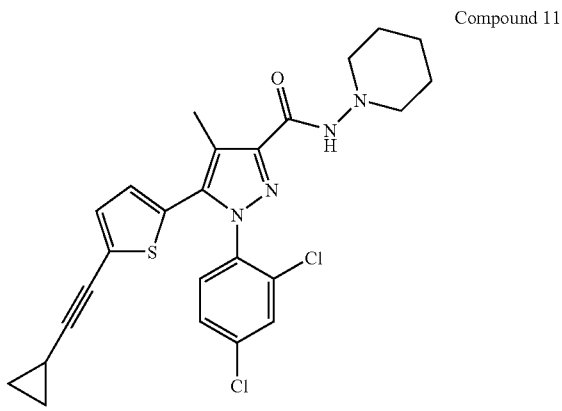
Compound 12
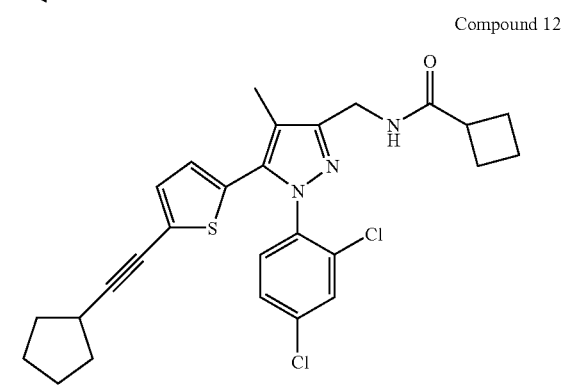
-continued
Compound 13
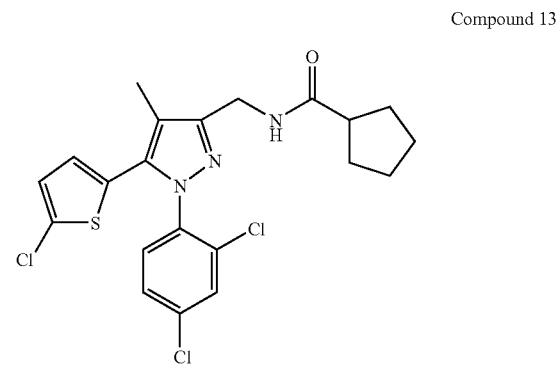
Compound 14
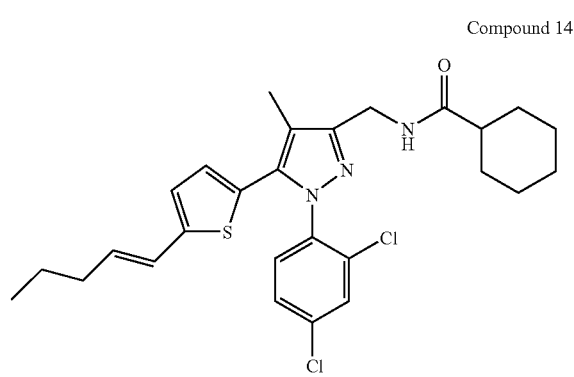
Compound 15
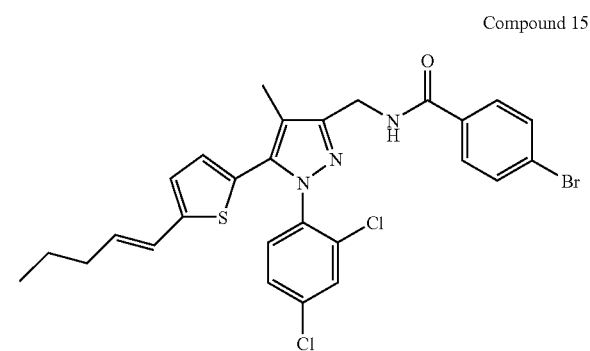
Compound 16
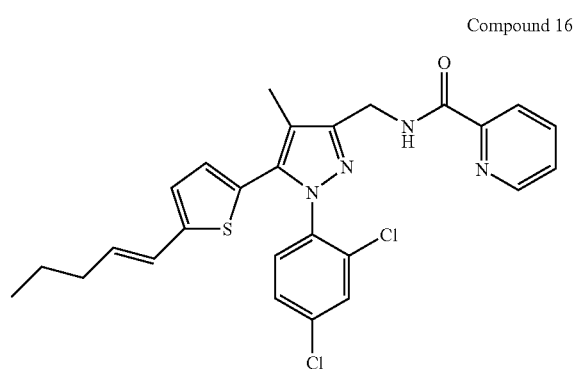

-continued
Compound 17
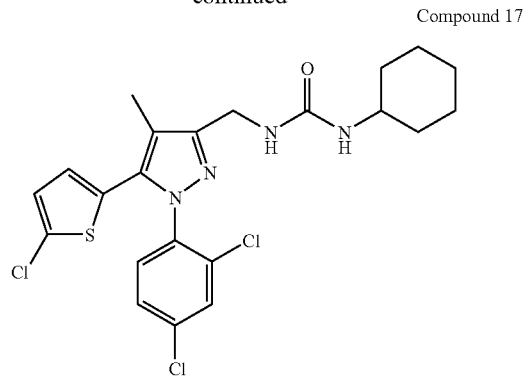
Compound 21
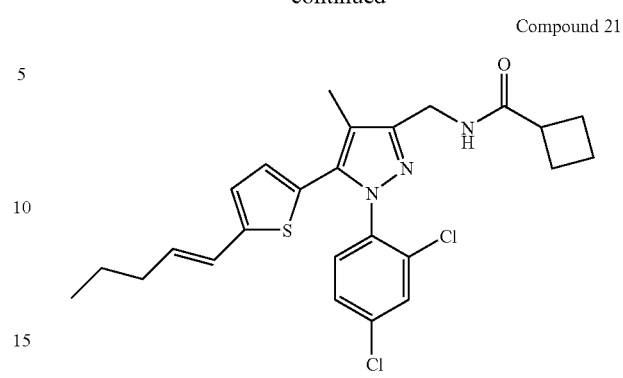
Compound 18
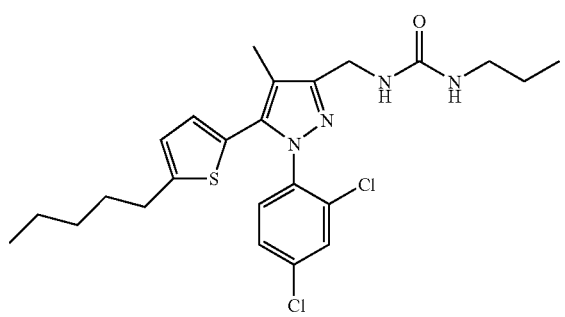
Compound 22
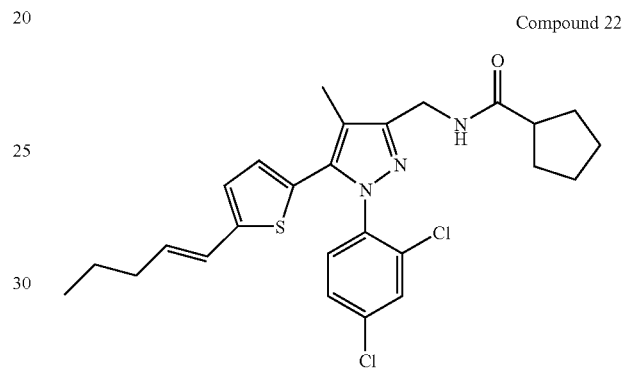
Compound 19
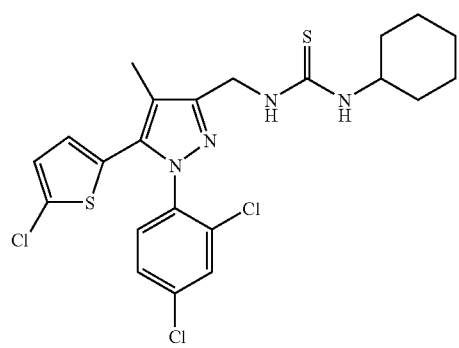
Compound 23
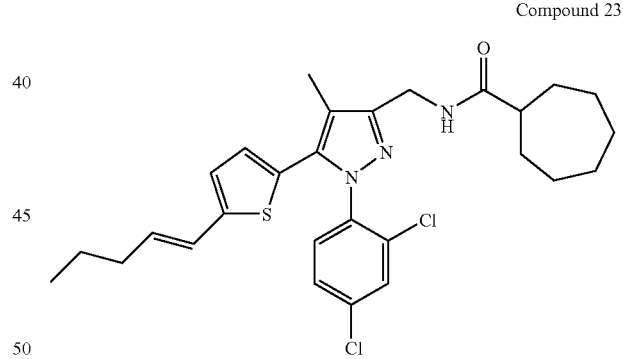
Compound 20
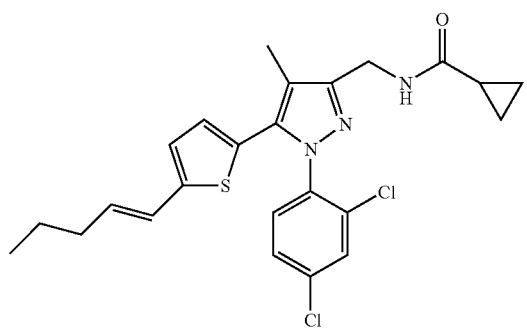
Compound 24
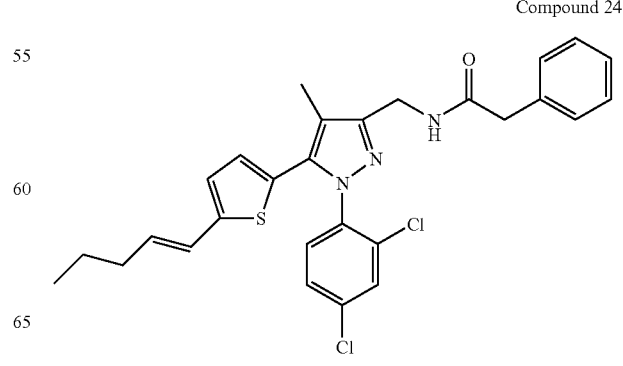

-continued
Compound 25
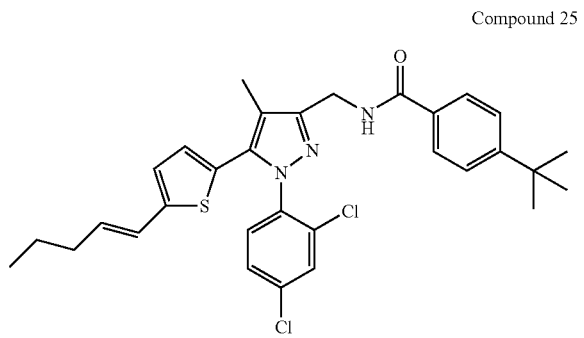
Compound 26
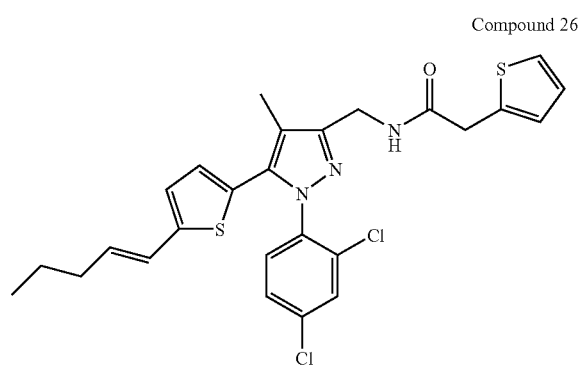
Compound 27
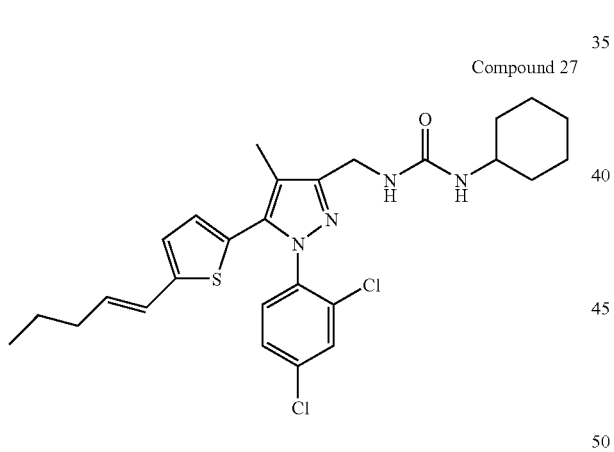
Compound 28
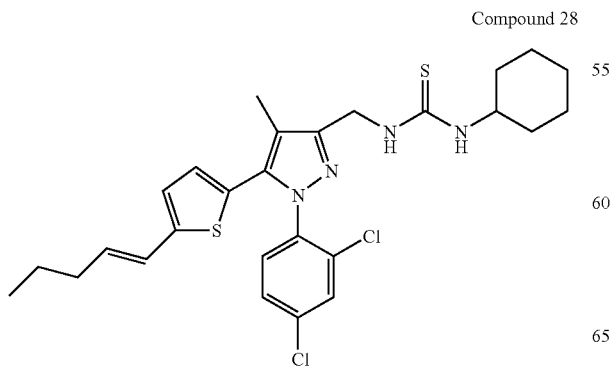
-continued
Compound 29
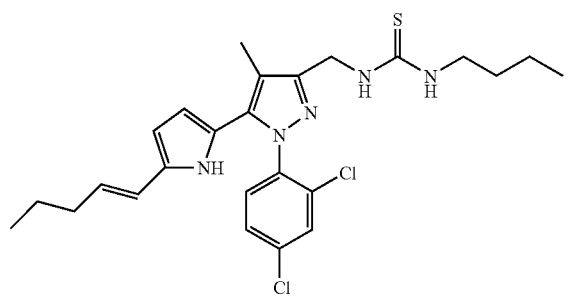
Compound 30
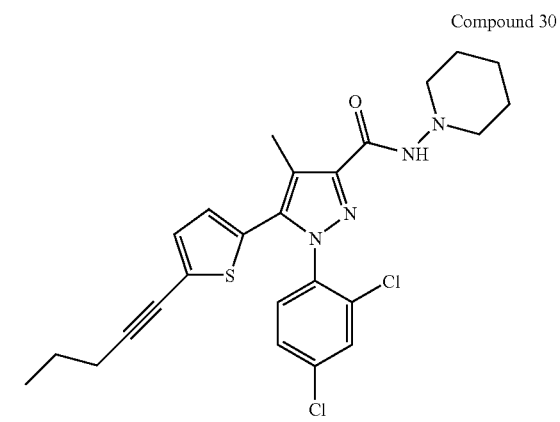
Compound 31
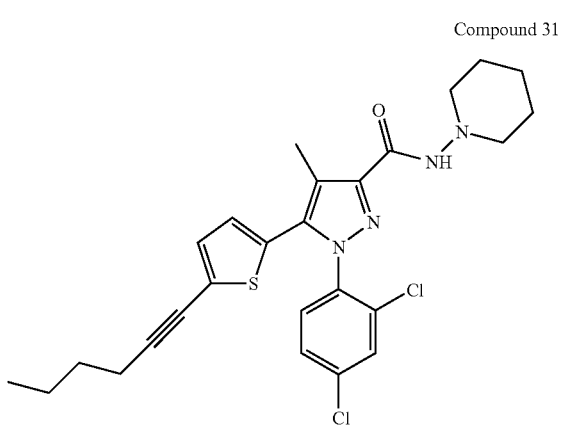
Compound 32
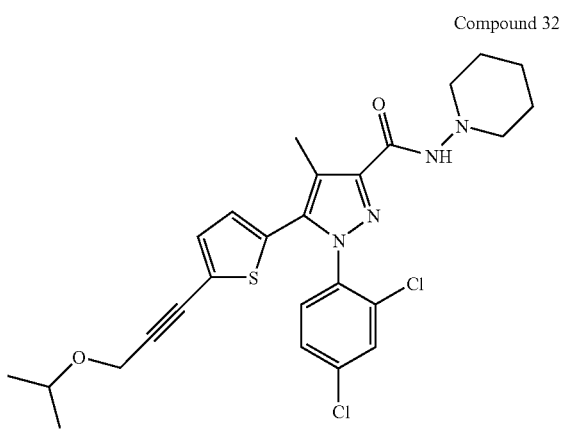

Compound 33
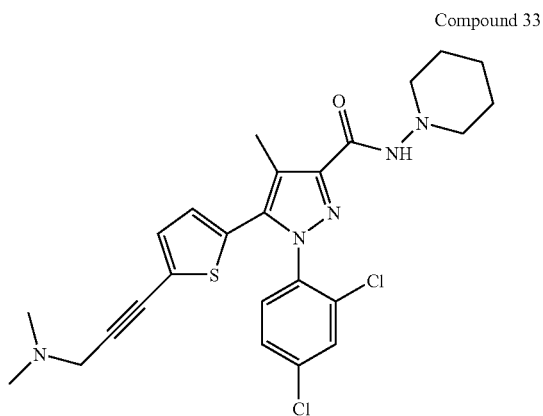
Compound 34
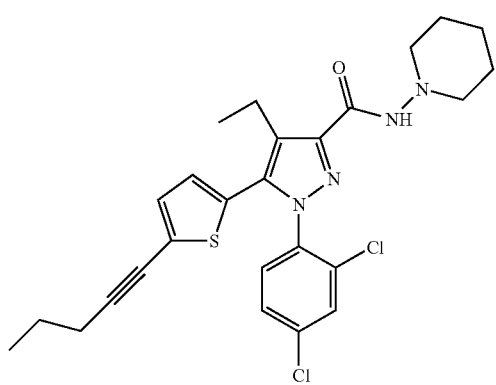
Compound 35
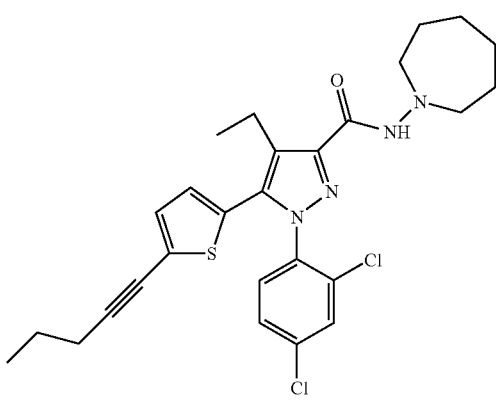
Compound 36
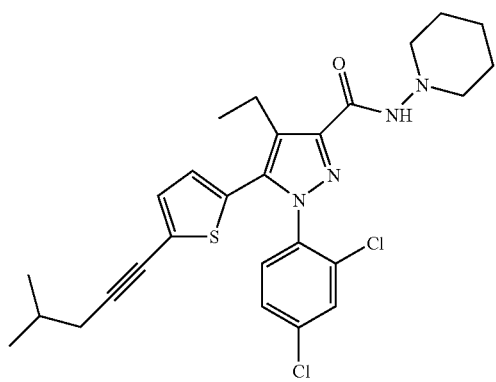
Compound 37
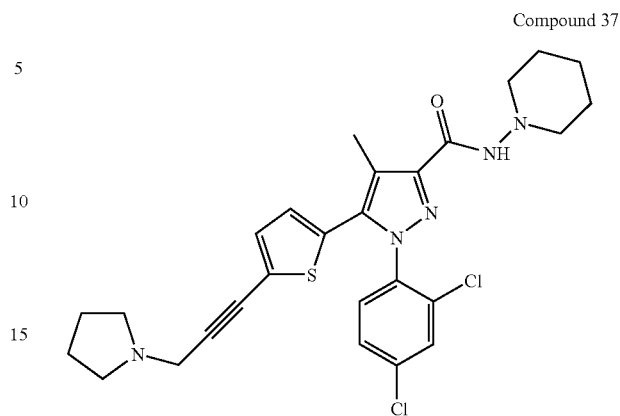
Compound 38
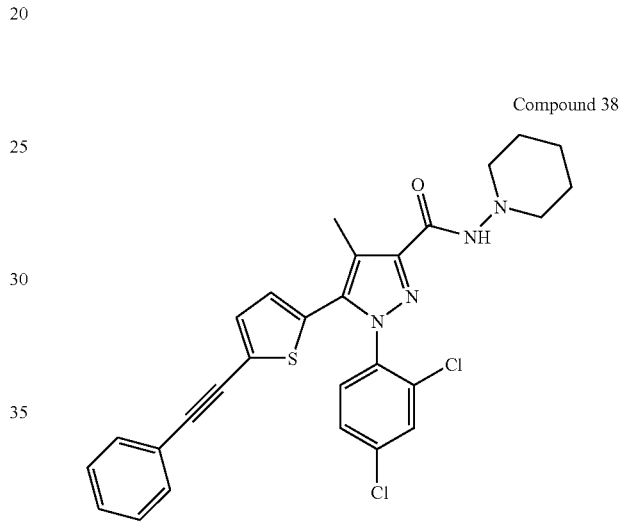
The thiophene compounds described above can be prepared by methods well known in the art. Examples 1-38 below provide detailed descriptions of how compounds 1-38 were actually prepared.
Scheme I shown below illustrates a typical synthetic route for synthesizing certain exemplary compounds.
Scheme I
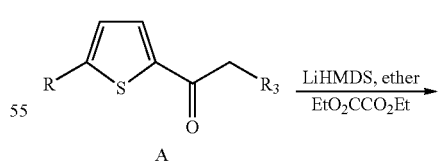
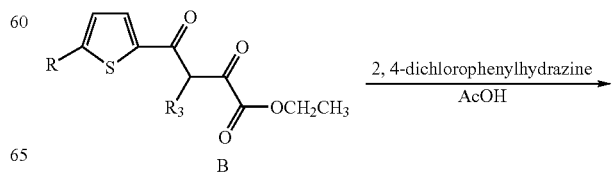

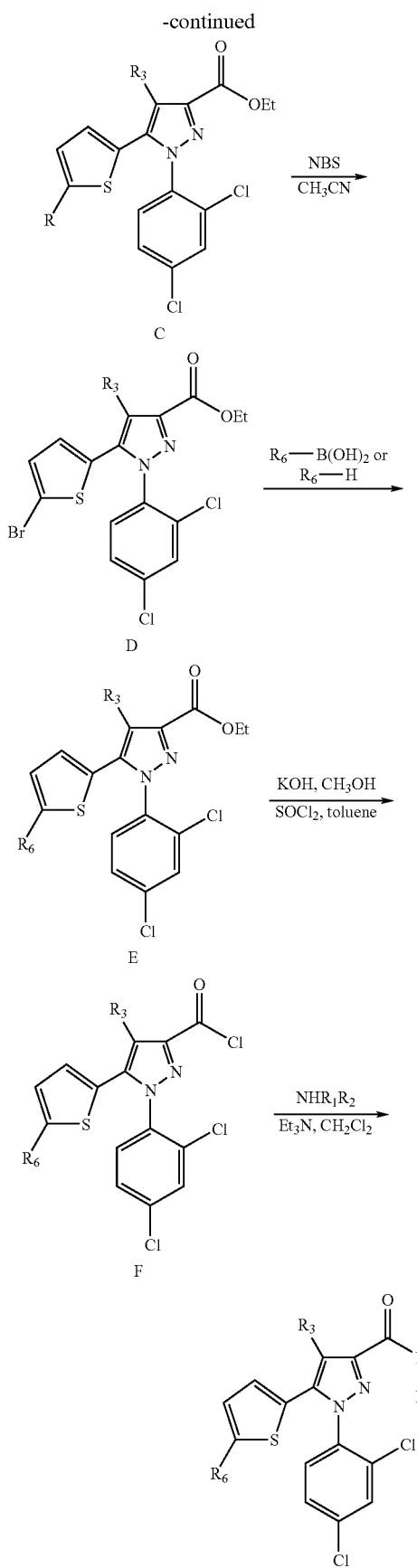

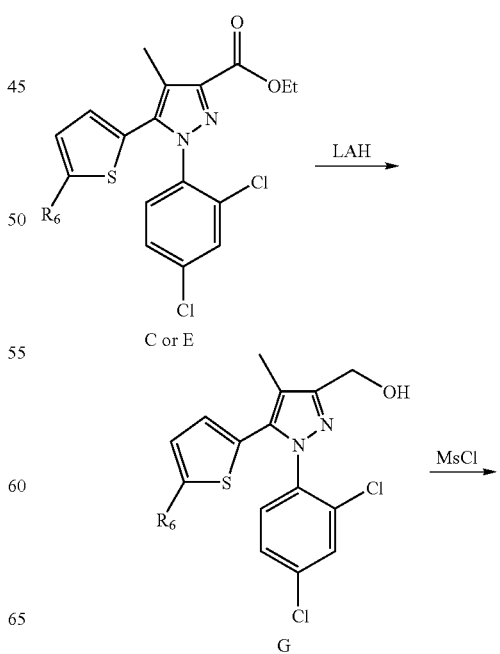

Compounds 1-11 and 30-38:
R = H or Cl;
$R_3$ = methyl or ethyl;
$R_6$ = penten-1-yl, 2-cyclohexylethen-1-yl, 2-cyclopentylethyn-1-yl, 2-cyclohexylethyn-1-yl, 2-cyclopropylethyn-1-yl, pent-1-ynyl, hex-1-ynyl, 3-isopropoxy-prop-1-ynyl, 3-dimethylamino-prop-1-ynyl, pyrolidin1-1-yl-propyn-1-yl, or phenylethyn-1-yl;
$R_a$ = H; and
$R_b$ = cyclohexyl, piperidinyl, or octahydrocyclopentapyrrolyl; or
$R_a$ and $R_b$ = piperidinyl or pyrrolidinyl.

Specifically, as shown in Scheme 1 above, a thiophene compound containing a ketone group (e.g., compound A) can first undergo a Claisen condensation reaction with an oxalate compound (e.g., diethyl oxalate) in the presence of a lithium salt to form a 1,3-dione compound containing an ester group (e.g., compound B). The 1,3-dione compound can then react with a hydrazine to afford a corresponding hydrazone, which, without purification, is allowed to undergo intramolecular cyclization under refluxing acetic acid to form a pyrazole compound (e.g., compound C) containing an ester group. The pyrazole compound can be treated with N-bromosuccinimide in acetonitrile to form a compound containing a bromide group at the 5-position on the thiophene ring (e.g. compound D). The bromide group can then be replaced with an alkenyl or alkynyl group by reacting with a substituted boronic acid or an alkyne. The ester group on the compound thus formed (e.g., compound E) can subsequently be hydrolyzed in the presence of a base to form a carboxyl group, which in turn can be converted to an acyl chloride group by reacting with thionyl chloride to form an acyl chloride compound (e.g., compound F). The acyl chloride compound can then react with various amines to form compounds of the invention (e.g., Compounds 1-11 and 30-38).

The intermediates mentioned in Scheme I above can be modified in various manners to afford other compounds of this invention. An example is illustrated in Scheme II below:

Scheme II

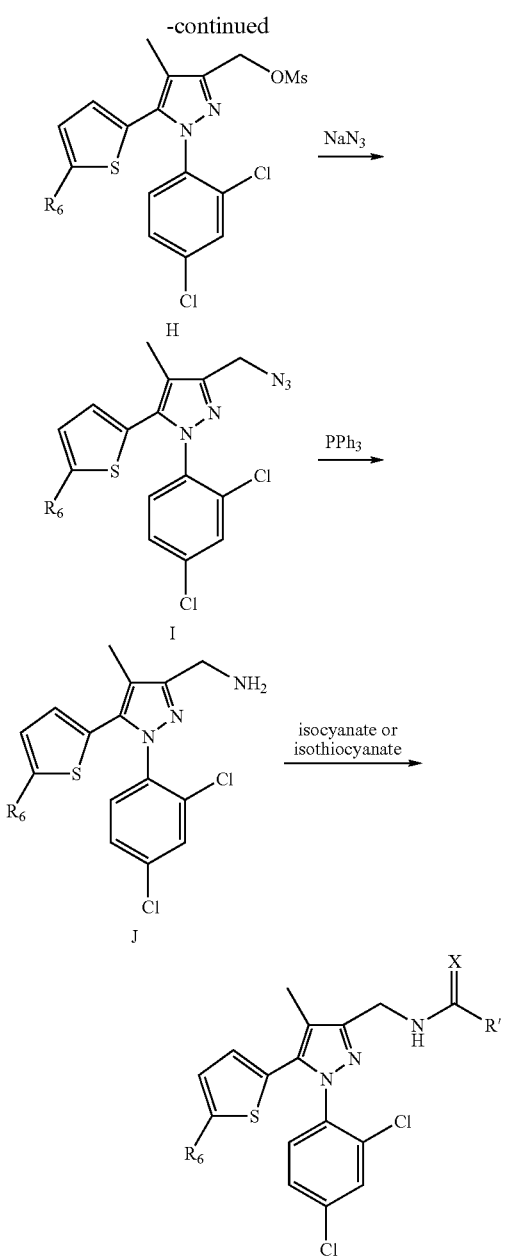

Compounds 12-29:
X = O or S; R$_6$ = Cl or penten-1-yl;
R' = cycloprpyl, cyclobutyl, cyclopentyl, cyclohexyl, cycloheptyl, pyridyl, phenyl substituted with bromo or isobutyl, methyl substituted with phenyl or thienyl, amino substituted with cyclohexyl or propyl.

As shown in Scheme II below, the ester group on compound C or E can be reduced to a hydroxyl group. The compound thus formed (e.g., compound G) can then react with methanesulfonyl chloride to form a compound with a methanesulfonyl acid ester group (e.g., compound H). The resultant compound can react with sodium azide to form a compound having an azido group (e.g., compound I), which can then be converted to a compound having an amino group (e.g., compound J). The compound thus formed can reacting with acyl chlorides, isocyanates, or isothiocyanates to form other compounds of invention (e.g., compounds 12-29).

A thiophene compound synthesized above can be purified by a suitable method such as column chromatography, high-pressure liquid chromatography, or recrystallization.

Other thiophene compounds can be prepared using other suitable starting materials through the above synthetic routes and others known in the art. The methods described above may also additionally include steps, either before or after the steps described specifically herein, to add or remove suitable protecting groups in order to ultimately allow synthesis of the thiophene compounds. In addition, various synthetic steps may be performed in an alternate sequence or order to give the desired compounds. Synthetic chemistry transformations and protecting group methodologies (protection and deprotection) useful in synthesizing applicable thiophene compounds are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The thiophene compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition containing an effective amount of at least one thiophene compound described above and a pharmaceutical acceptable carrier. Further, this invention covers a method of administering an effective amount of one or more of the thiophene compounds to a patient having a disease described in the summary section above. "An effective amount" refers to the amount of an active thiophene compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having one or more thiophene compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active thiophene compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active thiophene compound. Examples of other carriers include colloidal silicon oxide, magnesium stearate, cellulose, sodium lauryl sulfate, and D&C Yellow #10.

The thiophene compounds described above can be preliminarily screened for their efficacy in treating above-described diseases by an in vitro assay (Example 39 below) and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Preparation of Compound 1: (E)-1-(2,4-dichlorophenyl)-4-methyl-5-(5-(pent-1-enyl)thiophen-2-yl)-N-(piperidin-1-yl)-1H-pyrazole-3-carboxamide To a magnetically stirred solution of lithium bis(trimethylsilyl)amide (46.7 mL, 46.7 mmol) in diethyl ether (55 mL) was added a solution of 1-(2-thienyl)-1-propanone (6.0 g, 42.53 mmol) in diethyl ether (30 mL) at −78° C. After the mixture was stirred at the same temperature for an additional 45 minutes, diethyl oxalate (6.9 mL, 51.03 mmol) was added to the mixture. The reaction mixture was allowed to warm to room temperature and stirred for another 16 hours. The precipitate was filtered, washed with diethyl ether, and dried under vacuum to afford Intermediate I(a), i.e., a lithium salt of ethyl 3-methyl-2,4-dioxo-4-thiophen-2-yl-butanonate (6.14 g, 62%).

To a magnetically stirred solution of Intermediate I(a) (4.65 g, 18.84 mmol) in (56 mL) of ethanol was added 2,4-dichlorophenylhydrazine hydrochloride (4.35 g, 20.73 mmol) in one portion at room temperature. The resulting mixture was stirred at room temperature for 24 hours. The precipitate thus obtained was filtered, washed with ethanol and diethyl ether, and then dried under vacuum to give a light yellow solid (5.18 g, 71%). This solid was redissolved in acetic acid (30 mL) and heated under reflux for 24 hours. The mixture was poured into ice water and extracted with ethyl acetate. The extracts were combined, washed with water, saturated aqueous sodium bicarbonate, and brine, dried over anhydrous sodium sulfate, filtered, and concentrated by evaporation. The crude product thus obtained was purified by flash column chromatography on silica gel with n-hexane/ethyl acetate (9:1) to give Intermediate II(a), i.e., 1-(2,4-Dichloro-phenyl)-4-methyl-5-thiophen-2-yl-1H-pyrazole-3-carboxylic acid ethyl ester, as a white solid (3.87 g, 73%).

NBS (3.2 g, 16.6 mmol) in small portions was added to a magnetically stirred solution of Intermediate II(a) (5.27 g, 13.8 mmol) in acetonitrile at 0° C. After stirring the mixture for 1 hour at 0° C., a saturated aqueous sodium sulfite solution was added. The organic solvent was then evaporated and the residual mixture was extracted with ethyl acetate. The extracts were combined, washed with water, saturated aqueous sodium bicarbonate, and brine, dried over anhydrous sodium sulfate, filtered, and concentrated. The crude product was purified by flash chromatography on silica gel with n-hexane/ethyl acetate (9:1) to give Intermediate III, i.e., 5-(5-Bromo-thiophen-2-yl)-1-(2,4-dichloro-phenyl)-4-methyl-1H-pyrazole-3-carboxylic acid ethyl ester, as a white solid (4.91 g, 77%).

A solution of Intermediate III (2.28 g, 4.96 mmol), pent-1-enylboronic acid (677.8 mg, 5.95 mmol), tetrakis-triphenylphosphinopallidum (572.8 mg, 0.57 mmol), and cesium carbonate (3.23 g, 9.91 mmol) in DME (10 mL) was refluxed for 3 hours. After the solvent was evaporated under reduced pressure, the resultant residue was purified by flash column chromatography with n-hexane/ethyl acetate (5:1) to give Intermediate IV(a), i.e., 1-(2,4-Dichloro-phenyl)-4-methyl-5-[((E)-5-pent-1-enyl)-thiophen-2-yl]-1H-pyrazole-3-carboxylic acid ethyl ester, as a white solid (1.16 g, 73%).

To a magnetically stirred solution of Intermediate IV(a) (230.2 mg, 0.48 mmol) in methanol (3.0 mL) was added a solution of potassium hydroxide (160.1 mg, 3.0 mmol) in methanol (7 mL). After the mixture was refluxed for 3 hours, it was cooled, poured into water, and acidified with a 10% hydrochloric acid aqueous solution. The precipitate thus obtained was filtered, washed with water, and dried under vacuum to give Intermediate V(a), i.e., 1-(2,4-Dichloro-phenyl)-4-methyl-5-[((E)-5-pent-1-enyl)-thiophen-2-yl]-1H-pyrazole-3-carboxylic acid, as a white solid (191.1 mg, 92%).

A solution of Intermediate V(a) (171.7 mg, 0.41 mmol) and thionyl chloride (114.1 µL, 1.56 mmol) in toluene (7.0 mL) was refluxed for 3 hours. After the solvent was evaporated under reduced pressure, the resultant residue was redissolved in toluene (7.0 mL) and evaporated again to yield the crude corresponding carboxylic chloride as a white solid. The carboxylic chloride was dissolved in dichloromethane (10 mL) and added dropwise to a mixture of 1-aminopiperidine (53.9 µL, 0.54 mmol) and triethylamine (75.8 µL, 0.54 mmol) in 5 mL of dichloromethane at 0° C. After the mixture was stirred at room temperature for 8 hours, the reaction was quenched with water. The aqueous layer was separated and extracted with dichloromethane (2×20 mL). The extracts were combined, washed with brine, dried over anhydrous sodium sulfate, filtered, and concentrated under reduced pressure. The crude product thus obtained was purified by flash column chromatography on silica gel with n-hexane/ethyl acetate (2:1) to give Compound 1 as a white solid (172.8 mg, 84%).

$^1$H-NMR (CDCl$_3$, ppm): 7.61 (d, 1H), 7.49 (d, 1H), 7.35-7.33 (m, 2H), 6.71 (d, 1H), 6.64 (d, 1H), 6.39 (d, 1H), 6.02 (dt, 1H), 2.87-2.84 (m, 4H), 2.50-2.45 (m, 3H), 1.79-1.71 (m, 6H), 1.50-1.40 (m, 4H), 0.93 (t, 3H).

ES-MS (M+1): 503.1.

Example 2

Preparation of Compound 2: (E)-1-(2,4-dichlorophenyl)-N-(hexahydrocyclopenta[c]pyrrol-2(1H)-yl)-4-methyl-5-(5-(pent-1-enyl)thiophen-2-yl)-1H-pyrazole-3-carboxamide Compound 2 was prepared in a manner similar to that described in Example 1 except that, in the last step, the crude carboxylic chloride (75 mg, 0.17 mmol) was treated with hexahydrocyclopenta-[c]pyrrol-2(1H)-amine hydrochloride (44.0 mg, 0.27 mmol), and triethylamine (62.9 µL, 0.44 mmol) in dichloromethane at 0° C. Compound 2 was obtained as a white solid (68 mg, 75%).

$^1$H-NMR (CDCl$_3$, ppm): 7.48 (s, 1H), 7.32 (m, 2H), 6.71 (d, 1H), 6.64 (dd, 1H), 6.38 (dd, 1H), 6.01 (dt, 1H), 3.28 (t, 2H), 2.67 (m, 2H), 2.54-2.47 (m, 5H), 2.16-2.07 (m, 2H), 1.67-1.42 (m, 9H), 0.93 (t, 3H).

ES-MS (M+1): 529.1.

Example 3

Preparation of Compound 3: (E)-N-cyclohexyl-1-(2,4-dichlorophenyl)-4-methyl-5-(5-(pent-1-enyl)thiophen-2-yl)-1H-pyrazole-3-carboxamide Compound 3 was prepared in a manner similar to that described in Example 1 except that, in the last step, the crude carboxylic chloride (88.5 mg, 0.20 mmol) was treated with cyclohexyl amine (49.4 µL, 0.44 mmol) and triethylamine (70.4 µL, 0.49 mmol) in dichloromethane at 0° C. Compound 3 was obtained as a white solid (78.4 mg, 77%).

$^1$H-NMR (CDCl$_3$, ppm): 7.49 (s, 1H), 7.34 (m, 2H), 6.79 (d, 1H), 6.72 (d, 1H), 6.64 (d, 1H), 6.39 (dt, 1H), 2.49 (t, 3H), 2.10 (m, 2H), 2.12-1.72 (m, 2H), 1.66-1.14 (m, 12H), 0.95 (t, 3H).

ES-MS (M+1): 502.1.

Example 4

Preparation of Compound 4: (E)-(1-(2,4-dichlorophenyl)-4-methyl-5-(5-(pent-1-enyl)thiophen-2-yl)-1H-pyrazol-3-yl)(piperidin-1-yl)methanone Compound 4 was prepared in a manner similar to that described in Example 1 except that, in the last step, the crude carboxylic chloride (93.2 mg, 0.21 mmol) was treated with piperidine (45.3 µL, 0.40 mmol) and triethylamine (63.2 µL, 0.44 mmol) in dichloromethane at 0° C. Compound 4 was obtained as a white solid (80.3 mg, 78%).

$^1$H-NMR (CDCl$_3$, ppm): 7.49 (s, 1H), 7.30 (m, 2H), 6.72 (d, 1H), 6.64 (d, 1H), 6.41 (d, 1H), 6.03 (dt, 1H), 3.75 (m, 2H), 3.64 (m, 2H), 2.29 (t, 3H), 2.14 (m, 2H), 1.74-1.60 (m, 6H), 1.54-1.42 (m, 2H), 0.94 (t, 3H).

ES-MS (M+1): 488.1.

Example 5

Preparation of Compound 5: (E)-(1-(2,4-dichlorophenyl)-4-methyl-5-(5-(pent-1-enyl)thiophen-2-yl)-1H-pyrazol-3-yl)(pyrrolidin-1-yl)methanone Compound 5 was prepared in a manner similar to that described in Example 1 except that, in the last step, the crude carboxylic chloride (101.4 mg, 0.23 mmol) was treated with pyrrolidine (43.8 µL, 0.39 mmol) and triethylamine (63.6 µL, 0.44 mmol) in dichloromethane at 0° C. Compound 5 was obtained as a white solid (84.2 mg, 77%).

$^1$H-NMR (CDCl$_3$, ppm): 7.49 (m, 1H), 7.30 (m, 2H), 6.72 (d, 1H), 6.64 (d, 1H), 6.39 (d, 1H), 6.02 (dt, 1H), 3.80 (m, 2H), 3.66 (m, 2H), 2.38 (t, 3H), 2.12 (m, 2H), 1.92 (m, 4H), 1.46 (m, 2H), 0.93 (t, 3H).

ES-MS (M+1): 474.1.

Example 6

Preparation of Compound 6: (E)-5-(5-(2-cyclohexylvinyl)thiophen-2-yl)-1-(2,4-dichlorophenyl)-N-(hexahydrocyclopenta[c]pyrrol-2(1H)-yl)-4-methyl-1H-pyrazole-3-carboxamide Intermediate IV(b), i.e., 5-[5-((E)-2-cyclohexyl-vinyl)-thiophen-2-yl]-1-(2,4-dichloro-phenyl)-4-methyl-1H-pyrazole-3-carboxylic acid ethyl ester, was prepared in a manner similar to Intermediate IV(a) was prepared in Example 1 except that pent-1-enylboronic acid was replaced with (E)-2-cyclohexyl-vinylboronic acid. Intermediate IV(b) was obtained as a white solid in 80% yield.

Intermediate V(b), i.e., 5-[5-((E)-2-cyclohexyl-vinyl)-thiophen-2-yl]-1-(2,4-dichloro-phenyl)-4-methyl-1H-pyrazole-3-carboxylic acid, was prepared in a manner similar to Intermediate V(a) described in Example 1 except that Intermediate IV(a) was replaced with Intermediate IV(b) (269.4 mg, 0.55 mmol). Intermediate V(b) was obtained as a white solid in 90% yield.

Compound 6 was prepared in a manner similar to that described in Example 1 except that, in the last step, a crude carboxylic chloride (96 mg, 0.20 mmol) obtained from Intermediate V(b) was treated with hexahydrocyclopenta-[c]pyrrol-2(1H)-amine hydrochloride (62.8 mg, 0.39 mmol) and triethylamine (63.6 µL, 0.44 mmol) in dichloromethane at 0° C. Compound 6 was obtained as a white solid (79 mg, 72%).

$^1$H-NMR (CDCl$_3$, ppm): 7.47 (m, 1H), 7.32 (m, 2H), 6.72 (d, 1H), 6.63 (d, 1H), 6.39 (d, 1H), 6.00 (dt, 1H), 3.25 (m, 2H), 2.63 (brs, 2H), 2.47 (m, 2H), 2.48 (s, 3H) 1.81-1.12 (m, 18H).

ES-MS (M+1): 569.2.

Example 7

Preparation of Compound 7: 5-(5-(cyclopropylethynyl)thiophen-2-yl)-1-(2,4-dichlorophenyl)-4-methyl-N-(piperidin-1-yl)-1H-pyrazole-3-carboxamide To a suspension of Intermediate III (230 mg, 0.5 mmol) prepared in Example 1, PdCl$_2$(PPh$_3$)$_2$ (11 mg, 0.015 mmol), and CuI (2 mg, 0.02 mmol) in THF (3 mL) were added ethynyl-cyclopropane (40 mg, 0.6 mmol) and a 0.5 M aqueous solution of 2-ethanolamine (3 mL). The resultant mixture was heated at 60° C. for 6 hours. After the mixture was cooled to room temperature, it was poured into a mixed solvent of water (20 mL) and diethyl ether (20 mL). The aqueous layer was extracted and the combined organic layer was concentrated to give the crude residue, which was purified by flash column chromatography with n-hexane/ethyl acetate (5:1) to afford Intermediate IV(c), i.e., 5-(5-Cyclopropylethynyl-thiophen-2-yl)-1-(2,4-dichloro-phenyl)-4-methyl-1H-pyrazole-3-carboxylic acid ethyl ester, as a colorless oil (202.4 mg, 91%).

Intermediate V(c), i.e., 5-(5-cyclopropylethynyl-thiophen-2-yl)-1-(2,4-dichloro-phenyl)-4-methyl-1H-pyrazole-3-carboxylic acid, was prepared in a manner similar to Intermediate V(a) described in Example 1 except that Intermediate IV(a) was replaced with Intermediate IV(c) (366.2 mg, 0.88 mmol). Intermediate V(c) was obtained as a white solid in 88% yield.

Compound 7 was prepared in a manner similar to that described in Example 1 except that, in the last step, a crude carboxylic chloride (110.3 mg, 0.25 mmol) prepared from Intermediate V(c) was treated with 1-amino-piperidine (50.2 mg, 0.50 mmol), and triethylamine (84.1 µL, 0.60 mmol) in dichloromethane at 0° C. Compound 7 was obtained as a white solid (94.3 mg, 75%).

$^1$H-NMR (CDCl$_3$, ppm): 7.48 (d, 1H), 7.33 (d, 2H), 6.95 (d, 1H), 6.68 (d, 1H), 3.26 (t, 4H), 2.46 (s, 3H), 1.80-1.65 (m, 4H), 1.50-1.38 (m, 2H).

ES-MS (M+1): 499.2.

Example 8

Preparation of Compound 8: 5-(5-(cyclopentylethynyl)thiophen-2-yl)-1-(2,4-dichlorophenyl)-N-(hexahydrocyclopenta[c]pyrrol-2(1H)-yl)-4-methyl-1H-pyrazole-3-carboxamide Intermediate IV(d), i.e., 5-(5-cyclopentylethynyl-thiophen-2-yl)-1-(2,4-dichloro-phenyl)-4-methyl-1H-pyrazole-3-carboxylic acid ethyl ester, was prepared in a manner similar to Intermediate IV(c) described in Example 7 except that ethynyl-cyclopropane was replaced with ethynyl-cyclopentane. Intermediate IV(d) was obtained as a white solid in 88% yield.

Intermediate V(d), i.e., 5-(5-cyclopentylethynyl-thiophen-2-yl)-1-(2,4-dichloro-phenyl)-4-methyl-1H-pyrazole-3-carboxylic acid, was prepared in a manner similar to Intermediate V(a) described in Example 1 except that Intermediate IV(a) was replaced with Intermediate IV(d) (387.2 mg, 0.87 mmol). Intermediate V(d) was obtained as a white solid in 87% yield.

Compound 8 was prepared in a manner similar to that described in Example 7 except that, in the last step, a crude carboxylic chloride (116.3 mg, 0.25 mmol) prepared from Intermediate V(d) was treated with hexahydrocyclopenta-[c]pyrrol-2(1H)-amine hydrochloride (82.4 mg, 0.51 mmol) and triethylamine (84.1 µL, 0.60 mmol) in dichloromethane at 0° C. Compound 8 was obtained as a white solid (102.1 mg, 74%).

$^1$H-NMR (CDCl$_3$, ppm): 7.48 (d, 1H), 7.35 (d, 2H), 6.95 (d, 1H), 6.67 (d, 1H), 3.26 (t, 2H), 2.80 (q, 1H), 2.66 (br, 1H), 2.50 (t, 2H), 2.46 (s, 3H), 2.02-1.84 (m, 2H), 1.81-1.40 (m, 12H), 1.26 (t, 2H).

ES-MS (M+1): 553.2.

Example 9

Preparation of Compound 9: 5-(5-(cyclohexylethynyl)thiophen-2-yl)-1-(2,4-dichlorophenyl)-N-(hexahydrocyclopenta[c]pyrrol-2(1H)-yl)-4-methyl-1H-pyrazole-3-carboxamide Intermediate IV(e), i.e., 5-(5-cyclohexylethynyl-thiophen-2-yl)-1-(2,4-dichloro-phenyl)-4-methyl-1H-pyrazole-3-carboxylic acid ethyl ester, was prepared in a manner similar to Intermediate IV(c) described in Example 7 except that ethynyl-cyclopropane was replaced with ethynyl-cyclohexane. Intermediate IV(e) was obtained as a white solid in 80% yield.

Intermediate V(e), i.e., 5-(5-cyclohexylethynyl-thiophen-2-yl)-1-(2,4-dichloro-phenyl)-4-methyl-1H-pyrazole-3-carboxylic acid, was prepared in a manner similar to Intermediate V(a) described in Example 1 except that Intermediate IV(a) was replaced with Intermediate IV(e) (384.3 mg, 0.84 mmol). Intermediate V(e) was obtained as a white solid in 87% yield.

Compound 9 was prepared in a manner similar to that described in Example 7 except that, in the last step, a crude carboxylic chloride (118.2 mg, 0.25 mmol) prepared from Intermediate V(e) was treated with hexahydrocyclopenta-[c]pyrrol-2(1H)-amine hydrochloride (82.3 mg, 0.51 mmol) and triethylamine (84.1 µL, 0.60 mmol) in dichloromethane at 0° C. Compound 9 was obtained as a white solid (106.2 mg, 77%).

$^1$H-NMR (CDCl$_3$, ppm): 7.48 (m, 1H), 7.39 (m, 2H), 7.32 (m, 2H), 6.96 (d, 1H), 6.67 (d, 1H), 3.24 (t, 2H), 2.63 (brs, 2H), 2.48 (s, 3H), 2.47 (m, 2H) 1.81-1.12 (m, 18H).

ES-MS (M+1): 567.2.

Example 10

Preparation of Compound 10: N-cyclohexyl-5-(5-(cyclopentylethynyl)-thiophen-2-yl)-1-(2,4-dichlorophenyl)-4-methyl-1H-pyrazole-3-carboxamide Compound 10 was prepared in a manner similar to that described in Example 8 except that, in the last step, the crude carboxylic chloride (116.2 mg, 0.25 mmol) was treated with cyclohexylamine (50.3 mg, 0.51 mmol) and triethylamine (84.1 µL, 0.60 mmol) in dichloromethane at 0° C. Compound 10 was obtained as a white solid (97.3 mg, 74%).

$^1$H-NMR (CDCl$_3$, ppm): 7.48 (brs, 1H), 7.33 (brs, 2H), 6.95 (d, 1H), 6.79 (d, 1H), 6.67 (d, 1H), 3.93 (q, 1H), 2.80 (q, 1H), 2.47 (s, 3H), 2.10-1.81 (m, 4H), 1.80-1.50 (m, 10H), 1.50-1.20 (m, 4H).

ES-MS (M+1): 526.2.

Example 11

Preparation of Compound 11: 5-(5-(cyclopentylethynyl)thiophen-2-yl)-1-(2,4-dichlorophenyl)-4-methyl-N-(piperidin-1-yl)-1H-pyrazole-3-carboxamide Compound 11 was prepared in a manner similar to that described in Example 8 except that, in the last step, the crude carboxylic chloride (90 mg, 0.21 mmol) with 1-amino-piperidine (42 mg, 0.42 mmol) and triethylamine (63.8 µL, 0.44 mmol) in dichloromethane at 0° C. Compound 11 was obtained as a white solid (75.3 mg, 70%).

$^1$H-NMR (CDCl$_3$, ppm): 7.60 (br, 1H), 7.49 (brs, 1H), 7.34 (brs, 2H), 6.96 (d, 1H), 6.68 (d, 1H), 2.92-3.76 (m, 5H), 2.46 (s, 3H), 2.02-1.82 (m, 2H), 1.81-1.50 (m, 10H), 1.45-1.25 (m, 2H).

ES-MS (M+1): 527.2.

Example 12

Preparation of Compound 12: N-((5-(5-chlorothiophen-2-yl)-1-(2,4-dichlorophenyl)-4-methyl-1H-pyrazol-3-yl)methyl)cyclobutanecarboxamide Intermediate I(b), i.e., a lithium salt of ethyl 3-methyl-2,4-dioxo-4-(5-chloro-thiophen-2-yl)-butanonate, was prepared in 42% yield in a manner similar to Intermediate I(a) described in Example 1 except that 1-(2-thienyl)-1-ethanone was replaced with 1-(5-chloro-2-thienyl)-1-propanone.

Intermediate II(b), i.e., 5-(5-chloro-thiophen-2-yl)-1-(2,4-dichloro-phenyl)-4-methyl-1H-pyrazole-3-carboxylic acid ethyl ester, was prepared from Intermediate I(b) in a manner similar to Intermediate II(a) as a white solid in 50% yield.

Lithium aluminum hydride (291.9 mg, 3.10 mmol) was added to a magnetically stirred solution of Intermediate II(b) (644.4 mg, 1.55 mmol) in THF (20 mL) at 0° C. After the mixture was stirred at the same temperature for 30 minutes, the reaction was quenched with water. The aqueous layer was separated and extracted with ethyl acetate (2×20 mL). The extracts were combined, washed with brine, dried over anhydrous sodium sulfate, filtered, concentrated, and then purified by chromatography on silica gel to give compound VI(a), i.e., [5-(5-chloro-thiophen-2-yl)-1-(2,4-dichloro-phenyl)-4-methyl-1H-pyrazol-3-yl]-methanol, as a colorless liquid (509.5 mg, 88%).

Triethylamine (300 µL, 2.1 mmol) was added to a magnetically stirred solution of Intermediate VI(a) (419.2 mg, 1.02 mmol) in THF (10 mL) at 0° C. After the mixture was stirred at the same temperature for 30 minutes, methanesulfonyl chloride (200 µL, 1.74 mmol) was added. The mixture was then stirred at room temperature for 8 hours. The reaction was quenched with water and the aqueous layer was separated and extracted with ethyl acetate (2×50 mL). The extracts were combined, washed with brine, dried over anhydrous sodium sulfate, filtered, and evaporated. The crude product thus obtained was purified by flash column chromatography on silica gel with n-hexane/ethyl acetate (4:1) to give Intermediate VII(a), i.e., methanesulfonic acid 5-(5-chloro-thiophen-2-yl)-1-(2,4-dichloro-phenyl)-4-methyl-1H-pyrazol-3-ylmethyl ester, as a colorless liquid (495 mg, 74%).

Sodium azide (135.1 mg, 2.22 mmol) in one portion was added to a magnetically stirred solution of Intermediate VII(a) (272.2 mg, 0.61 mmol) in DMF (20 mL). The reaction mixture was heated at 80° C. for 3 hours. After the mixture was cooled, the reaction was quenched with water and the aqueous layer was separated and extracted with ethyl acetate (2×30 mL). The extracts were combined, washed with brine, dried over anhydrous sodium sulfate, filtered, and concentrated. The crude product thus obtained was purified by flash column chromatography on silica gel with n-hexane/ethyl acetate (3:1) to give Intermediate VIII(a), i.e., 3-azidomethyl-5-(5-chloro-thiophen-2-yl)-1-(2,4-dichloro-phenyl)-4-methyl-1H-pyrazole, as a colorless liquid (230.3 mg, 83%).

Triphenylphosphine (166.9 mg, 0.62 mmol) and water (2 mL) were sequentially added to a magnetically stirred solution of Intermediate VIII(a) (230.2 mg, 0.57 mmol) in THF (10 mL). After the mixture was stirred at room temperature for 48 hours, the reaction was extracted with ethyl acetate (2×10 mL). The extracts were combined, washed with brine, dried over anhydrous sodium sulfate, filtered, and concentrated. The crude product thus obtained was purified by flash column chromatography on silica gel with ethyl acetate/methanol (4:1) to give Intermediate IX(a), i.e., (5-(5-chlorothiophen-2-yl)-1-(2,4-dichlorophenyl)-4-methyl-1H-pyrazol-3-yl)methanamine, as a white solid (209.8 mg, 97%).

To a magnetically stirred solution of Intermediate IX(a) (40.1 mg, 0.10 mmol) in dichloromethane were added triethylamine (20 µL, 0.13 mmol) and cyclobutanecarbonyl chloride (15 µL, 0.09 mmol) sequentially. After the mixture was stirred at room temperature for 8 hours, the reaction was quenched with water and the aqueous layer was separated and extracted with dichloromethane (2×10 mL). The extracts were combined, washed with brine, dried over anhydrous sodium sulfate, filtered, and concentrated. The crude product thus obtained was purified by flash column chromatography on silica gel with n-hexane/ethyl acetate (3:1) to give Compound 12 as a white solid (24.9 mg, 51%).

$^1$H-NMR (CDCl$_3$, ppm): 7.49 (d, 1H), 7.33 (d, 1H), 7.32 (s, 1H), 6.80 (d, 1H), 6.61 (d, 1H), 6.01 (brs, 1H), 4.51 (d, 2H), 3.05 (m, 1H), 2.38-2.25 (m, 2H), 2.21-2.11 (m, 2H), 2.14 (s, 3H), 1.82-2.05 (m, 2H).

ES-MS (M+1): 454.0.

Example 13

Preparation of Compound 13: N-((5-(5-chlorothiophen-2-yl)-1-(2,4-dichlorophenyl)-4-methyl-1H-pyrazol-3-yl)methyl)cyclopentanecarboxamide Compound 13 was prepared in a manner similar to that described in Example 12 except that, in the last step, Intermediate IX(a) (51.6 mg, 0.11 mmol) was treated with triethylamine (20 µL, 0.13 mmol) and cyclopentanecarbonyl chloride (15 µL, 0.11 mmol). Compound 13 was obtained as a white solid (32.1 mg, 64%).

$^1$H-NMR (CDCl$_3$, ppm): 7.49 (d, 1H), 7.33 (d, 1H), 7.32 (s, 1H), 6.80 (d, 1H), 6.61 (d, 1H), 6.11 (brs, 1H), 4.52 (d, 2H), 2.60-2.52 (m, 1H), 2.15 (s, 3H), 1.90-1.70 (m, 8H).

ES-MS (M+1): 468.

Example 14

Preparation of Compound 14: (E)-N-((1-(2,4-dichlorophenyl)-4-methyl-5-(5-(pent-1-enyl)thiophen-2-yl)-1H-pyrazol-3-yl)methyl)cyclohexanecarboxamide Intermediate VI(b), i.e., {1-(2,4-dichlorophenyl)-4-methyl-5-[((E)-5-pent-1-enyl)-thiophen-2-yl]-1H-pyrazol-3-yl}-methanol, was prepared in a manner similar to Intermediate VI(a) described in Example 12 except that Intermediated II(b) used therein was replaced with Intermediate IV(a) (886.2 mg, 1.97 mmol) prepared in Example 1. Intermediate VI(b) was obtained as a colorless liquid in 50% yield.

Intermediate VII(b), i.e., methanesulfonic acid 1-(2,4-dichloro-phenyl)-4-methyl-5-[((E)-5-pent-1-enyl)-thiophen-2-yl]-1H-pyrazol-3-ylmethyl ester, was prepared from Intermediate VI(b) (842 mg, 3.27 mmol) in a manner similar to Intermediate VII(a) described in Example 12 as a colorless liquid in 73% yield.

Intermediate VIII(b), i.e., 3-azidomethyl-1-(2,4-dichlorophenyl)-4-methyl-5-[((E)-5-pent-1-enyl)-thio-phen-2-yl]-1H-pyrazole, was prepared from Intermediate VII(b) (741.1 mg, 1.52 mmol) in a manner similar to Intermediate VIII(a) described in Example 12 as a colorless liquid in 60% yield.

Intermediate IX(b), i.e., (E)-(1-(2,4-dichlorophenyl)-4-methyl-5-(5-(pent-1-enyl)thiophen-2-yl)-1H-pyrazol-3-yl)methanamine, was prepared from Intermediate VIII(b) (400.2 mg, 0.92 mmol) in a manner similar to Intermediate IX(a) described in Example 12 as a colorless liquid in 73% yield.

Compound 14 was prepared in a manner similar to that described in Example 12 except that, in the last step, Intermediate IX(b) (40.3 mg, 0.10 mmol) was treated with triethylamine (20 μL, 0.13 mmol) and cyclohexanecarbonyl chloride (20 μL, 0.14 mmol). Compound 14 was obtained as a white solid (41.0 mg, 78%).

$^1$H-NMR (CDCl$_3$, ppm): 7.45 (d, 1H), 7.27 (d, 1H), 7.25 (s, 1H), 7.12 (d, 1H), 6.70 (d, 1H), 6.65 (t, 1H), 6.60 (d, 1H), 6.39 (d, 1H), 6.01 (dt, 1H), 4.52 (d, 2H), 2.16 (s, 3H), 2.16-2.02 (m, 2H), 1.80-1.65 (m, 4H), 1.53-1.40 (m, 4H), 1.27-1.15 (m, 4H), 0.92 (t, 3H).

ES-MS (M+1): 516.2.

Example 15

Preparation of Compound 15: (E)-4-bromo-N-((1-(2, 4-dichlorophenyl)-4-methyl-5-(5-(pent-1-enyl)thiophen-2-yl)-1H-pyrazol-3-yl)methyl)benzamide Compound 15 was prepared in a manner similar to that described in Example 14 except that, in the last step, Intermediate IX(b) (60.5 mg, 0.15 mmol) was treated with triethylamine (50 μL, 0.33 mmol) and 4-bromobenzoyl chloride (39.2 mg, 0.18 mmol). Compound 15 was obtained as a white solid (45.2 mg, 51%).

$^1$H-NMR (CDCl$_3$, ppm): 7.70 (m, 2H), 7.57 (m, 2H), 7.48 (d, 1H), 7.32 (d, 2H), 6.93 (m, 1H), 6.72 (d, 1H), 6.62 (d, 1H), 6.40 (d, 1H), 6.01 (dt, 1H), 4.70 (d, 2H), 2.22 (s, 3H), 2.17-2.10 (m, 2H), 1.51-1.41 (m, 2H), 0.92 (t, 3H).

ES-MS (M+23): 610.1.

Example 16

Preparation of Compound 16: (E)-N-((1-(2,4-dichlorophenyl)-4-methyl-5-(5-(pent-1-enyl)thiophen-2-yl)-1H-pyrazol-3-yl)methyl)picolinamide Compound 16 was prepared in a manner similar to that described in Example 14 except that, in the last step, Intermediate IX(b) (59.8 mg, 0.14 mmol) was treated with triethylamine (50 μL, 0.33 mmol) and pyridine 2-carbonyl chloride (32.2 mg, 0.17 mmol). Compound 16 was obtained as a white solid (52.1 mg, 74%).

$^1$H-NMR (CDCl$_3$, ppm): 8.54 (m, 1H), 8.23 (m, 1H), 7.83 (m, 1H), 7.46 (m, 1H), 7.46-7.27 (m, 3H), 6.71 (d, 1H), 6.61 (d, 1H), 6.39 (d, 1H), 6.01 (dt, 1H), 4.76 (d, 2H), 2.22 (s, 3H), 2.16-2.09 (m, 2H), 1.49-1.39 (m, 2H), 0.93 (t, 3H).

ES-MS (M+1): 511.2.

Example 17

Preparation of Compound 17: 1-((5-(5-chlorothiophen-2-yl)-1-(2,4-dichlorophenyl)-4-methyl-1H-pyrazol-3-yl)methyl)-3-cyclohexylurea Isocyanatocyclohexane (20 μL, 0.14 mmol) was added to a magnetically stirred solution of Intermediate IX(a) (40.3 mg, 0.11 mmol) prepared in Example 12 in THF. After the mixture was stirred at room temperature for 8 hours, the solvent was evaporated. The crude product thus obtained was purified by flash column chromatography on silica gel with n-hexane/ethyl acetate (1:1) to give Compound 17 as a white solid (33.2 mg, 62%).

$^1$H-NMR (CDCl$_3$, ppm): 7.48 (d, 1H), 7.35 (d, 2H), 7.30 (s, 1H), 6.80 (d, 1H), 6.60 (d, 1H), 4.85 (m, 1H), 4.46 (m, 1H), 4.41 (d, 2H), 3.55 (m, 1H), 2.17 (s, 3H), 1.91 (m, 2H), 1.67 (m, 2H), 1.40-1.07 (m, 5H).

ES-MS (M+1): 497.1.

Example 18

Preparation of Compound 18: (E)-1-((1-(2,4-dichlorophenyl)-4-methyl-5-(5-(pent-1-enyl)thiophen-2-yl)-1H-pyrazol-3-yl)methyl)-3-propylurea Compound 18 was prepared in a manner similar to that described in Example 14 except that Intermediate IX(b) (60.2 mg, 0.14 mmol) was treated with n-propylisocyanate (50.2 μL, 0.33 mmol). Compound 18 was obtained as a white solid (55.3 mg, 70%).

$^1$H-NMR (CDCl$_3$, ppm): 7.45 (d, 1H), 7.29 (m, 2H), 6.70 (d, 1H), 6.59 (d, 1H), 6.39 (d, 1H), 6.01 (dt, 1H), 5.63 (t, 1H), 5.18 (t, 1H), 4.38 (d, 2H), 3.05 (m, 2H), 2.19-2.09 (m, 2H), 2.17 (s, 3H), 1.52-1.26 (m, 4H), 0.89 (t, 3H), 0.87 (t, 3H).

ES-MS (M+1): 491.2.

Example 19

Preparation of Compound 19: 1-((5-(5-chlorothiophen-2-yl)-1-(2,4-dichlorophenyl)-4-methyl-1H-pyrazol-3-yl)methyl)-3-cyclohexylthiourea Compound 19 was prepared in a manner similar to that described in Example 17 except that Intermediate IX(a) (40.3 mg, 0.11 mmol) was treated with isothiocyanatocyclohexane (20 μL, 0.14 mmol). Compound 19 was obtained as a white solid (39.8 mg, 76%).

$^1$H-NMR (CDCl$_3$, ppm): 7.53 (m, 1H), 7.35 (m, 1H), 7.33 (m, 1H), 6.82 (m, 1H), 6.63 (m, 1H), 6.49 (brs, 1H), ), 4.60 (brs, 1H), 2.18 (s, 3H), 1.98 (m, 2H), 1.62 (m, 5H), 1.39-1.07 (m, 6H).

ES-MS (M+1): 513.0.

Example 20

Preparation of Compound 20: (E)-N-((1-(2,4-dichlorophenyl)-4-methyl-5-(5-(pent-1-enyl)thiophen-2-yl)-1H-pyrazol-3-yl)methyl)cyclopropanecarboxamide Compound 20 was prepared in a manner similar to that described in Example 14 except that, in the last step, Intermediate IX(b) (33 mg, 0.08 mmol) was treated with triethylamine (20 μL, 0.14 mmol) and cyclopropanecarbonyl chloride (15 μL, 0.11 mmol). Compound 20 was obtained as a white solid (18 mg, 47%).

$^1$H-NMR (CDCl$_3$, ppm): 7.48 (m, 1H), 7.32 (d, 2H), 6.71 (d, 1H), 6.60 (d, 1H), 6.46 (brs, 1H), 6.41 (d, 1H), 6.01 (dt, 1H), 4.54 (d, 2H), 2.18 (s, 3H), 2.15 (m, 2H), 1.41 (m, 3H), 0.98 (m, 2H), 0.94 (t, 3H), 0.74 (m, 2H).

ES-MS (M+1): 474.1.

Example 21

Preparation of Compound 21: (E)-N-((1-(2,4-dichlorophenyl)-4-methyl-5-(5-(pent-1-enyl)thiophen-2-yl)-1H-pyrazol-3-yl)methyl)cyclobutanecarboxamide Compound 21 was prepared in a manner similar to that described in Example 14 except that, in the last step, Intermediate IX(b) (48 mg, 0.12 mmol) was treated with triethylamine (20 μL, 0.14 mmol) and cyclobutanecarbonyl chloride (20 μL, 0.19 mmol). Compound 21 was obtained as a white solid (33 mg, 57%).

¹H-NMR (CDCl₃, ppm): 7.47 (m, 1H), 7.31 (d, 2H), 6.71 (d, 1H), 6.60 (d, 1H), 6.39 (d, 1H), 6.15 (brs, 1H), 6.01 (dt, 1H), 4.51 (d, 2H), 3.05 (m, 1H), 2.29 (m, 2H), 2.18 (s, 3H), 2.15 (m, 4H), 1.96 (m, 2H), 1.46 (m, 2H), 0.93 (t, 3H).
ES-MS (M+1): 488.1.

Example 22

Preparation of Compound 22: (E)-N-((1-(2,4-dichlorophenyl)-4-methyl-5-(5-(pent-1-enyl)thiophen-2-yl)-1H-pyrazol-3-yl)methyl)cyclopentanecarboxamide Compound 22 was prepared in a manner similar to that described in Example 14 except that, in the last step, Intermediate IX(b) (48 mg, 0.12 mmol) was treated with triethylamine (20 μL, 0.14 mmol) and cyclopentanecarbonyl chloride (20 μL, 0.17 mmol). Compound 22 was obtained as a white solid (41 mg, 69%).
¹H-NMR (CDCl₃, ppm): 7.47 (m, 1H), 7.31 (brs, 2H), 6.71 (d, 1H), 6.60 (d, 1H), 6.39 (d, 1H), 6.26 (brs, 1H), 6.01 (dt, 1H), 4.52 (d, 2H), 2.56 (m, 1H), 2.17 (s, 3H), 2.14 (m, 2H), 1.91-1.64 (m, 7H), 1.54 (m, 1H), 1.45 (m, 2H), 0.91 (t, 3H).
ES-MS (M+1): 502.1.

Example 23

Preparation of Compound 23: (E)-N-((1-(2,4-dichlorophenyl)-4-methyl-5-(5-(pent-1-enyl)thiophen-2-yl)-1H-pyrazol-3-yl)methyl)cycloheptanecarboxamide Compound 23 was prepared in a manner similar to that described in Example 14 except that, in the last step, Intermediate IX(b) (52 mg, 0.13 mmol) was treated with triethylamine (20 μL, 0.14 mmol) and cycloheptanecarbonyl chloride (29 μL, 0.20 mmol). Compound 23 was obtained as a white solid (43 mg, 62%).
¹H-NMR (CDCl₃, ppm): 7.18 (m, 1H), 7.01 (brs, 2H), 6.41 (d, 1H), 6.30 (d, 1H), 6.09 (d, 1H), 5.98 (m, 1H), 5.72 (dt, 1H), 4.20 (d, 2H), 1.95 (m, 1H), 1.87 (s, 3H), 1.85 (m, 2H), 1.60 (m, 2H), 1.52-1.29 (m, 4H), 1.32-1.07 (m, 8H), 0.63 (t, 3H).
ES-MS (M+1): 530.3.

Example 24

Preparation of Compound 24: (E)-N-((1-(2,4-dichlorophenyl)-4-methyl-5-(5-(pent-1-enyl)thiophen-2-yl)-1H-pyrazol-3-yl)methyl)-2-phenylacetamide Compound 24 was prepared in a manner similar to that described in Example 14 except that, in the last step, Intermediate IX(b) (60 mg, 0.15 mmol) was treated with triethylamine (50 μL, 0.36 mmol) and phenylacetyl chloride (30 μL, 0.23 mmol). Compound 24 was obtained as a white solid (42 mg, 54%).
¹H-NMR (CDCl₃, ppm): 7.45 (d, 1H), 7.34-7.21 (m, 7H), 6.70 (d, 1H), 6.57 (d, 1H), 6.38 (d, 1H), 6.19 (brs, 1H), 6.01 (dt, 1H), 4.49 (d, 2H), 3.59 (s, 2H), 2.12 (s, 3H), 2.10 (m, 2H), 1.46 (m, 2H), 0.93 (s, 3H).
ES-MS (M+1): 524.2.

Example 25

Preparation of Compound 25: (E)-4-tert-butyl-N-((1-(2,4-dichlorophenyl)-4-methyl-5-(5-(pent-1-enyl)thiophen-2-yl)-1H-pyrazol-3-yl)methyl)benzamide Compound 25 was prepared in a manner similar to that described in Example 14 except that, in the last step, Intermediate IX(b) (60 mg, 0.15 mmol) was treated with triethylamine (50 μL, 0.36 mmol) and 4-tert-butylbenzoyl chloride (35 μL, 0.18 mmol). Compound 25 was obtained as a white solid (43 mg, 51%).
¹H-NMR (CDCl₃, ppm): 7.74 (d, 2H), 7.40 (s, 1H), 7.39 (d, 2H), 7.25 (m, 2H), 6.70 (d, 1H), 6.60 (d, 1H), 6.38 (d, 1H), 6.01 (dt, 1H), 4.74 (d, 2H), 2.24 (s, 3H), 2.12 (m, 2H), 1.44 (m, 2H), 1.31 (s, 9H), 0.93 (s, 3H).
ES-MS (M+1): 566.2.

Example 26

Preparation of Compound 26: (E)-N-((1-(2,4-dichlorophenyl)-4-methyl-5-(5-(pent-1-enyl)thiophen-2-yl)-1H-pyrazol-3-yl)methyl)-2-(thiophen-2-yl)acetamide Compound 26 was prepared in a manner similar to that described in Example 14 except that, in the last step, Intermediate IX(b) (60 mg, 0.15 mmol) was treated with triethylamine (50 μL, 0.36 mmol) and 2-thiopheneacetyl chloride (20 μL, 0.16 mmol). Compound 26 was obtained as a white solid (45 mg, 57%).
¹H-NMR (CDCl₃, ppm): 7.45 (d, 1H), 7.26 (m, 1H), 7.27 (d, 2H), 7.19 (m, 1H), 6.93 (m, 1H), 6.70 (d, 1H), 6.59 (d, 1H), 6.54 (brs, 1H), 6.38 (d, 1H), 6.01 (dt, 1H), 4.51 (d, 2H), 3.79 (s, 2H), 2.20-2.01 (m, 2H), 2.12 (s, 3H), 1.45 (m, 2H), 0.93 (s, 3H).
ES-MS (M+1): 530.2.

Example 27

Preparation of Compound 27: (E)-1-cyclohexyl-3-((1-(2,4-dichlorophenyl)-4-methyl-5-(5-(pent-1-enyl)thiophen-2-yl)-1H-pyrazol-3-yl)methyl)urea Compound 27 was prepared in a manner similar that described in Example 14 except that Intermediate IX(b) (33 mg, 0.08 mmol) was treated with cyclohexyl isocyanate (15 μL, 0.12 mmol). Compound 27 was obtained as a white solid (21 mg, 49%).
¹H-NMR (CDCl₃, ppm): 7.46 (m, 1H), 7.29 (m, 2H), 6.71 (d, 1H), 6.59 (d, 1H), 6.39 (d, 1H), 6.01 (dt, 1H), 5.25 (m, 1H), 4.74 (d, 1H), 4.39 (d, 2H), 3.54 (m, 1H), 2.18 (s, 3H), 2.14 (m, 2H), 1.98-1.80 (m, 3H), 1.69-1.22 (m, 7H), 1.07 (m, 2H), 0.93 (t, 3H).
ES-MS (M+1): 531.1.

Example 28

Preparation of Compound 28: (E)-1-cyclohexyl-3-((1-(2,4-dichlorophenyl)-4-methyl-5-(5-(pent-1-enyl)thiophen-2-yl)-1H-pyrazol-3-yl)methyl)thiourea Compound 28 was prepared in a manner similar that described in Example 14 except that Intermediate IX(b) (33 mg, 0.08 mmol) was treated with cyclohexyl isothiocyanate (15 μL, 0.11 mmol). Compound 28 was obtained as a white solid (29 mg, 65%).

¹H-NMR (CDCl₃, ppm): 7.48 (d, 1H), 7.31 (d, 2H), 6.98 (brs, 1H), 6.73 (d, 1H), 6.61 (d, 1H), 6.39 (d, 1H), 6.02 (dt, 1H), 4.57 (brs, 2H), 3.98 (brs, 1H), 2.19 (s, 3H), 2.15 (m, 2H), 1.95 (m, 2H), 1.71-1.24 (m, 9H), 1.16 (m, 2H), 0.93 (t, 3H).
ES-MS (M+1): 547.1.

Example 29

Preparation of Compound 29: (E)-1-butyl-3-((1-(2,4-dichlorophenyl)-4-methyl-5-(5-(pent-1-enyl)thiophen-2-yl)-1H-pyrazol-3-yl)methyl)thiourea Compound 29 was prepared in a manner similar that described in Example 14 except that Intermediate IX(b) (60 mg, 0.15 mmol) was treated with butyl isothiocyanate (20 μL, 0.19 mmol). Compound 29 was obtained as a white solid (44 mg, 57%).
¹H-NMR (CDCl₃, ppm): 7.48 (d, 1H), 7.30 (d, 2H), 6.81 (brs, 1H), 6.72 (d, 1H), 6.62 (d, 1H), 6.39 (d, 1H), 6.02 (dt, 1H), 4.58 (brs, 1H), 3.42 (brs, 2H), 2.19 (s, 3H), 2.14 (m, 2H), 1.61-1.24 (m, 8H), 0.93 (t, 3H), 0.85 (t, 3H).
ES-MS (M+1): 521.3.

Example 30

Preparation of Compound 30: 1-(2,4-Dichloro-phenyl)-4-methyl-5-(5-pent-1-ynyl-thiophen-2-yl)-1H-pyrazole-3-carboxylic acid piperidin-1-yl amide Intermediate IV(f), i.e., 1-(2,4-Dichloro-phenyl)-4-methyl-5-(5-pent-1-ynyl-thiophen-2-yl)-1H-pyrazole-3-carboxylic acid ethyl ester, was prepared in a manner similar to Intermediate IV(c) described in Example 7 except that ethynyl-cyclopropane was replaced with pent-1-yne. Intermediate IV(f) was obtained as a white solid in 94% yield.
Intermediate V(f), i.e., 1-(2,4-Dichloro-phenyl)-4-methyl-5-(5-pent-1-ynyl-thiophen-2-yl)-1H-pyrazole-3-carboxylic acid, was prepared in a manner similar to Intermediate V(a) described in Example 1 except that Intermediate IV(a) was replaced with Intermediate IV(f) (900 mg, 2.0 mmol). Intermediate V(f) was obtained as a white solid in 95% yield.
Compound 30 was prepared in a manner similar to that described in Example 7 except that, in the last step, crude carboxylic chloride (118.2 mg, 0.27 mmol) prepared from Intermediate V(f) was treated with 1-aminopiperidine (58 μL, 0.54 mmol) and triethylamine (95.3 μL, 0.68 mmol) in dichloromethane at 0° C. Compound 30 was obtained as a white solid (100.6 mg, 73%).
¹H NMR (CDCl₃, ppm): 7.62 (s, 1H), 7.41 (s, 1H), 7.36-7.26 (m, 2H), 6.90 (d, 1H), 6.63 (d, 1H), 2.90-2.70 (m, 4H), 2.40 (s, 3H), 2.30 (t, 2H), 1.78-1.60 (m, 1H), 1.62-1.48 (m, 2H), 1.41-1.28 (m, 2H), 0.94 (t, 3H).
ES-MS (M+1): 501.1.

Example 31

Preparation of Compound 31: 1-(2,4-dichlorophenyl)-5-(5-(hex-1-ynyl)thiophen-2-yl)-4-methyl-N-(piperidin-1-yl)-1H-pyrazole-3-carboxamide Intermediate IV(g), i.e., 1-(2,4-dichlorophenyl)-5-(5-(hex-1-ynyl)thiophen-2-yl)-4-methyl-1H-pyrazole-3-carboxylic acid ethyl ester, was prepared in a manner similar to Intermediate IV(c) described in Example 7 except that ethynyl-cyclopropane was replaced with hex-1-yne. Intermediate IV(g) was obtained as a white solid in 96% yield.
Intermediate V(g), i.e., 1-(2,4-dichlorophenyl)-5-(5-(hex-1-ynyl)thiophen-2-yl)-4-methyl-1H-pyrazole-3-carboxylic acid, was prepared in a manner similar to Intermediate V(a) described in Example 1 except that Intermediate IV(a) was replaced with Intermediate IV(g) (860 mg, 1.92 mmol). Intermediate V(g) was obtained as a white solid in 95% yield.
Compound 31 was prepared in a manner similar to that described in Example 7 except that, in the last step, a crude carboxylic chloride (108 mg, 0.24 mmol) prepared from Intermediate V(g) was treated with 1-aminopiperidine (52 μL, 0.48 mmol) and triethylamine (84 μL, 0.6 mmol) in dichloromethane at 0° C. Compound 31 was obtained as a white solid (90.4 mg, 73%).
¹H NMR (CDCl₃, ppm): 7.62 (s, 1H), 7.48 (s, 1H), 7.36-7.26 (m, 2H), 6.97 (d, 1H), 6.69 (d, 1H), 2.90-2.77 (m, 4H), 2.47 (s, 3H), 2.40 (t, 2H), 1.80-1.70 (m, 4H), 1.60-1.38 (m, 6H), 0.93 (t, 3H).
ES-MS (M+1): 515.1.

Example 32

Preparation of Compound 32: 1-(2,4-Dichloro-phenyl)-5-[5-(3-isopropoxy-prop-1-ynyl)-thiophen-2-yl]-4-methyl-1H-pyrazole-3-carboxylic acid piperidin-1-ylamide Intermediate IV(h), i.e., 1-(2,4-Dichloro-phenyl)-5-[5-(3-isopropoxy-prop-1-ynyl)-thiophen-2-yl]-4-methyl-1H-pyrazole-3-carboxylic acid ethyl ester, was prepared in a manner similar to Intermediate IV(c) described in Example 7 except that ethynyl-cyclopropane was replaced with 3-isopropoxy-prop-1-ynyl. Intermediate IV(h) was obtained as a white solid in 92% yield.
Intermediate V(h), i.e., 1-(2,4-Dichloro-phenyl)-5-[5-(3-isopropoxy-prop-1-ynyl)-thiophen-2-yl]-4-methyl-1H-pyrazole-3-carboxylic acid, was prepared in a manner similar to Intermediate V(a) described in Example 1 except that Intermediate IV(a) was replaced with Intermediate IV(h) (600 mg, 1.26 mmol). Intermediate V(f) was obtained as a white solid in 96% yield.
Compound 32 was prepared in a manner similar to that described in Example 7 except that, in the last step, a crude carboxylic chloride (300 mg, 0.64 mmol) prepared from Intermediate V(h) was treated with 1-aminopiperidine (128 μL, 1.2 mmol) and triethylamine (210 μL, 1.5 mmol) in dichloromethane at 0° C. Compound 32 was obtained as a white solid (238 mg, 70%).
¹H NMR (CDCl₃, ppm): 7.60 (s, 1H), 7.49 (d, 1H), 7.38-7.31 (m, 2H), 7.07 (d, 1H), 6.73 (d, 1H), 4.34 (s, 2H), 3.80 (q, 1H), 2.84 (t, 4H), 2.47 (s, 3H), 1.78-1.71 (m, 4H), 1.42-1.25 (m, 2H), 1.20 (d, 6H).
ES-MS (M+1): 531.1

Example 33

Preparation of Compound 33: 1-(2,4-Dichloro-phenyl)-5-[5-(3-dimethylamino-prop-1-ynyl)-thiophen-2-yl]-4-methyl-1H-pyrazole-3-carboxylic acid piperidin-1-ylamide Intermediate IV(i), i.e., 1-(2,4-Dichloro-phenyl)-5-[5-(3-dimethylamino-prop-1-ynyl)-thiophen-2-yl]-4-methyl-1H-pyrazole-3-carboxylic acid ethyl ester, was prepared in a manner similar to Intermediate IV(c) described in Example 7 except that ethynyl-cyclopropane was replaced with 3-dimethylamino-prop-1-ynyl. Intermediate IV(i) was obtained as a white solid in 97% yield.

Intermediate V(i), i.e., 1-(2,4-Dichloro-phenyl)-5-[5-(3-dimethylamino-prop-1-ynyl)-thiophen-2-yl]-4-methyl-1H-pyrazole-3-carboxylic acid, was prepared in a manner similar to Intermediate V(a) described in Example 1 except that Intermediate IV(a) was replaced with Intermediate IV(i) (500 mg, 1.15 mmol). Intermediate V(i) was obtained as a white solid in 92% yield.

Compound 33 was prepared in a manner similar to that described in Example 7 except that, in the last step, a crude carboxylic chloride (230 mg, 0.50 mmol) prepared from Intermediate V(i) was treated with 1-aminopiperidine (65 μL, 0.6 mmol) and triethylamine (100 μL, 0.72 mmol) in dichloromethane at 0° C. Compound 33 was obtained as a white solid (199 mg, 77%).

$^1$H NMR (CDCl$_3$, ppm): 7.60 (s, 1H), 7.50 (d, 1H), 7.36-7.30 (m, 2H), 7.04 (d, 1H), 6.71 (d, 1H), 3.45 (s, 2H), 2.90-2.80 (m, 4H), 2.48 (s, 3H), 2.33 (s, 6H), 1.80-1.68 (m, 4H), 1.50-1.40 (m, 2H).

ES-MS (M+1): 516.1.

Examples 34-36

Preparation of Compound 34: 1-(2,4-Dichloro-phenyl)-4-ethyl-5-(5-pent-1-ynyl-thiophen-2-yl)-1H-pyrazole-3-carboxylic acid piperidin-1-ylamide; Compound 35: 1-(2,4-Dichloro-phenyl)-4-ethyl-5-(5-pent-1-ynyl-thiophen-2-yl)-1H-pyrazole-3-carboxylic acid azepan-1-ylamide; and Compound 36: 1-(2,4-Dichloro-phenyl)-4-ethyl-5-[5-(4-methyl-pent-1-ynyl)-thiophen-2-yl]-1H-pyrazole-3-carboxylic acid piperidin-1-ylamide Compounds 34, 35, and 36 were prepared by procedures similar to that described in Example 7, using 1-(thiophen-2-yl)butan-1-one in place of 1-(thiophen-2-yl)propan-1-one.

Compound 34:
$^1$H-NMR (CDCl$_3$, ppm): 7.63 (s, 1H), 7.47 (dd, 1H), 7.34-7.32 (m, 2H), 6.96 (d, 1H), 6.67 (d, 1H), 2.91 (q, 2H), 2.90-2.78 (m, 4H), 2.38 (t, 2H), 1.80-1.70 (m, 4H), 1.60 (sextet, 2H), 1.48-1.36 (m, 2H), 1.25 (t, 3H), 1.02 (t, 3H).
ES-MS (M+1): 515.1.

Compound 35:
$^1$H-NMR (CDCl$_3$, ppm): 8.05 (s, 1H), 7.47 (s, 1H), 7.37-7.27 (m, 2H), 6.96 (d, 1H), 6.67 (d, 1H), 3.13 (t, 4H), 2.88 (q, 2H), 2.38 (t, 2H), 2.72 (t, 2H), 1.79-1.68 (m, 4H), 1.68-1.54 (m, 6H), 1.25 (t, 3H), 1.02 (t, 3H).
ES-MS (M+1): 529.1.

Compound 36:
$^1$H-NMR (CDCl$_3$, ppm): 7.64 (s, 1H), 7.47 (s, 1H), 7.33 (m, 2H), 6.96 (d, 1H), 6.66 (d, 1H), 2.92-2.83 (m, 6H), 2.29 (d, 2H), 1.94-1.86 (m, 1H), 1.78-1.72 (m, 4H), 1.46-1.38 (m, 2H), 1.25 (t, 3H), 1.01 (d, 6H).
ES-MS (M+1): 529.1.

Example 37

Preparation of Compound 37: 1-(2,4-Dichloro-phenyl)-4-methyl-5-[5-(3-pyrrolidin-1-yl-prop-1-ynyl)-thiophen-2-yl]-1H-pyrazole-3-carboxylic acid piperidin-1-ylamide Intermediate IV(j), i.e., 1-(2,4-Dichloro-phenyl)-4-methyl-5-[5-(3-pyrrolidin-1-yl-prop-1-ynyl)-thiophen-2-yl]-1H-pyrazole-3-carboxylic acid ethyl ester, was prepared in a manner similar to Intermediate IV(c) described in Example 7 except that ethynyl-cyclopropane was replaced with 1-Prop-2-ynyl-pyrrolidine. Intermediate IV(j) was obtained as a white solid in 94% yield.

Intermediate V(j), i.e., 1-(2,4-Dichloro-phenyl)-4-methyl-5-[5-(3-pyrrolidin-1-yl-prop-1-ynyl)-thiophen-2-yl]-1H-pyrazole-3-carboxylic acid, was prepared in a manner similar to Intermediate V(a) described in Example 1 except that Intermediate IV(a) was replaced with Intermediate IV(j) (300 mg, 0.65 mmol). Intermediate V(j) was obtained as a white solid in 96% yield.

Compound 37 was prepared in a manner similar to that described in Example 7 except that, in the last step, crude carboxylic chloride (180 mg, 0.38 mmol) prepared from Intermediate V(j) was treated with 1-aminopiperidine (49 μL, 0.46 mmol) and triethylamine (76 μL, 0.55 mmol) in dichloromethane at 0° C. Compound 37 was obtained as a white solid (167 mg, 81%).

1H NMR (CDCl$_3$, ppm): 7.59 (s, 1H), 7.47 (s, 1H), 7.38-7.30 (m, 2H), 7.01 (d, 1H), 6.69 (d, 1H), 3.59 (s, 2H), 2.90-2.76 (m, 4H), 2.72-2.56 (m, 4H), 2.46 (s, 3H), 1.84-1.62 (m, 8H), 1.44-1.34 (m, 2H).
ES-MS (M+1): 542.1.

Example 38

Preparation of Compound 38: 1-(2,4-Dichloro-phenyl)-4-methyl-5-(5-phenylethynyl-thiophen-2-yl)-1H-pyrazole-3-carboxylic acid piperidin-1-ylamide Intermediate IV(k), i.e., 1-(2,4-Dichloro-phenyl)-4-methyl-5-(5-phenylethynyl-thiophen-2-yl)-1H-pyrazole-3-carboxylic acid ethyl ester, was prepared in a manner similar to Intermediate IV(c) described in Example 7 except that ethynyl-cyclopropane was replaced with Ethynyl-benzene. Intermediate IV(k) was obtained as a white solid in 94% yield.

Intermediate V(k), i.e., 1-(2,4-Dichloro-phenyl)-4-methyl-5-(5-phenylethynyl-thiophen-2-yl)-1H-pyrazole-3-carboxylic acid, was prepared in a manner similar to Intermediate V(a) described in Example 1 except that Intermediate IV(a) was replaced with Intermediate IV(k) (300 mg, 0.63 mmol). Intermediate V(k) was obtained as a white solid in 93% yield.

Compound 38 was prepared in a manner similar to that described in Example 7 except that, in the last step, a crude carboxylic chloride (200 mg, 0.42 mmol) prepared from Intermediate V(k) was treated with 1-aminopiperidine (55 μL, 0.5 mmol) and triethylamine (84 μL, 0.6 mmol) in dichloromethane at 0° C. Compound 38 was obtained as a white solid (169 mg, 75%).

1H NMR (CDCl$_3$, ppm): 7.61 (s, 1H), 7.52-7.46 (m, 3H), 7.38-7.32 (m, 5H), 7.14 (d, 1H), 6.78 (d, 1H), 2.90-2.70 (m, 4H), 2.50 (s, 3H), 1.80-1.60 (m, 4H), 1.44-1.36 (m, 2H).
ES-MS (M+1): 535.1.

Example 39

In Vitro Assays

The affinity of 38 test compounds of this invention toward CB1 and CB2 receptors was determined by competitive radioligand binding in vitro assays. This method differentiates the binding strength between compounds by their abilities in displacing a receptor-specific radioactive ligand. Compounds with higher affinity than the radioactive ligand displace the ligand and bind to the receptors, while compounds with no affinity or lower affinity than the radioactive ligand do not. The readings of the radioactivity retained allow further analysis of receptor binding, and assist in predictions of the pharmacological activities of the test compounds.

In the assays, brain and spleen extracts from male Sprague-Dawley rats were respectively utilized as the source of CB1 and CB2 receptors. Male Sprague-Dawley rats weighing 175~200 g were used and housed under standard stalling conditions with food and water available ad libitum. The animals were sacrificed by cervical dislocation. Brain with cerebellum were excluded and spleen were dissected from the animals. The separated brain and spleen tissues were respectively homogenized by Polytron Homogenizers in 10 volumes of ice-cold buffer A (50 mM Tris, 5 mM $MgCl_2$, 2.5 mM EDTA, pH 7.4, 10% sucrose) with protease inhibitors. The homogenate was centrifuged for 15 minutes at 2,000×g at 4° C. The resultant supernatant was centrifuged again for 30 minutes at 43,000×g at 4° C. The final pellet was re-suspended in buffer A and stored at −80° C. The protein concentration of the purified membrane was determined by the Bradford method as described by the manual provided by Bio-Rad Laboratories, Inc., Hercules, Calif.

During the receptor binding experiments, 0.2~8 μg of a membrane was incubated with 0.75 nM [$^3$H]CP55,940 and a test compound in an incubation buffer (50 mM Tris-HCl, 5 mM $MgCl_2$, 1 mM EDTA, 0.3% BSA, pH 7.4). The non-specific binding was determined by using 1 μM of CP55,940. The mixture was incubated for 1.5 hours at 30° C. in Multiscreen microplates (Millipore, Billerica, Mass.). At the completion of the incubation, the reaction was terminated by Manifold filtration and washed with ice-cold wash buffer (50 mM Tris, pH 7.4, 0.25% BSA) four times. The radioactivity bound to the filters was measured by Topcount (Perkin Elmer Inc.). $IC_{50}$ values were calculated based on the concentration of the test compound required to inhibit 50% of the binding of [$^3$H]CP55,940.

The efficacy of each test compound was determined by DELFIA GTP-binding kit (Perkin Elmer Inc., Boston, Mass.). The DELFIA GTP-binding assay is a time-resolved fluorometric assay based on GDP-GTP exchange on G-protein subunits followed by activation of a G protein-coupled receptor by its agonists. Eu-GTP was used in this assay to allow monitoring of agonist-dependent activation of G-protein. Note that stimulation of CB1 receptor by CP55,940 leads to the replacement of GDP by GTP on the α-subunit of G-protein. The resultant GTP-Gα complex represents the activated form of G-protein. Eu-GTP, a non-hydrolysable analogue of GTP, can be used to quantify the amount of activated G-protein (Peltonen et al., Eur. J. Pharmacol. (1998) 355:275).

Plasma membrane of human CB1-expressing HEK293 cells was re-suspended in an assay buffer (50 mM HEPES, pH 7.4, 100 mM NaCl, 100 μg/mL saponin, 5 mM $MgCl_2$, 2 μM GDP, 0.5% BSA). An aliquot (4 μg protein/well) was added to each well of an AcroPlate (Pall Life Sciences, Ann Arbor, Mich.). After the addition of a test compound (various concentrations in 0.1% DMSO) and CP55,940 (20 nM in the assay buffer), the assay plate was incubated in the dark at 30° C. with slow shaking for 60 minutes. Eu-GTP was added to each well and the plate was incubated for another 35 minutes at 30° C. in the dark. The assay was terminated by washing the plate four times with a wash solution provided in the assay kit. Binding of the Eu-GTP was determined based on the fluorescence signal from a Victor 2 multi-label reader. The $IC_{50}$ value (i.e., 50% inhibition of CP55,940-stimulated Eu-GTP binding) for each test compound was determined by a concentration-response curve using nonlinear regression (Prism; GraphPad, San Diego, Calif.).

All of the test compounds showed $IC_{50}$ values between 0.1 nM and 20 μM in the CB1 receptor binding assays and/or CB2 receptor binding assays. The Eu-GTP binding assays were also conducted, and the results were comparable to those obtained from the above-mentioned radioligand binding assays.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

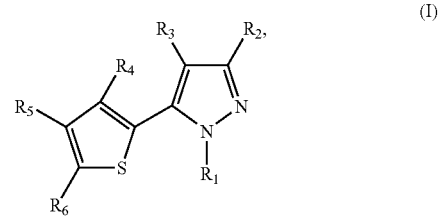

wherein
R$_1$ is H, C$_1$-C$_2$alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, or heteroaryl;

R$_2$ is H, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, heteroaryl, halo, OR$_a$, COOR$_a$, OC(O)R$_a$, C(O)R$_a$, C(O)NR$_a$R$_b$, or NR$_a$R$_b$, in which each of R$_a$ and R$_b$, independently, is H, C$_1$-C$_{10}$ alkyl, C$_3$-C$_{20}$ cycloalkyl, C$_1$-C$_{20}$ heterocycloalkyl, aryl, or heteroaryl;

R$_3$ is halo, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, or heteroaryl;

R$_4$ is H, halo, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, or heteroaryl;

R$_5$ is H, halo, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, or heteroaryl; or R$_5$, together with R$_6$ and the carbon atoms to which they are attached, is C$_3$-C$_{20}$ cycloalkenyl or C$_3$-C$_{20}$ heterocycloalkenyl; and R$_6$ is C$_2$-C$_{10}$ alkynyl substituted with alkoxy, amino, cycloalkyl, heterocycloalkyl, aryl, or heteroaryl.

2. The compound of claim 1, wherein R$_1$ is aryl substituted with halo.

3. The compound of claim 2, wherein R$_1$ is 2,4-dichlorophenyl.

4. A compound of formula (I):

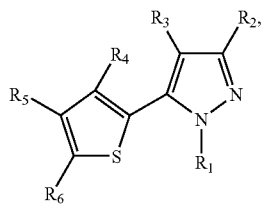

(I)

wherein

R₁ is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl;

R₂ is C(O)R$_a$, in which R$_a$ is piperidinyl or pyrrolidinyl, or C(O)NR$_a$R$_b$, in which each of R$_a$ and R$_b$, independently, is H, cyclohexyl, piperidinyl, or octahydrocyclopentapyrrolyl;

R₃ is halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl;

R₄ is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl;

R₅ is H, halo, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or R₅, together with R₆ and the carbon atoms to which they are attached, is $C_3$-$C_{20}$ cycloalkenyl or $C_3$-$C_{20}$ heterocycloalkenyl; and R₆ is $C_2$-$C_{10}$ alkenyl or $C_2$-$C_{10}$ alkynyl; or R₆, together with R₅ and the carbon atoms to which they are attached, is $C_3$-$C_{20}$ cycloalkenyl or $C_3$-$C_{20}$ heterocycloalkenyl.

5. A compound selected from compounds 7-11 and 30-38 shown, below:

Compound 7

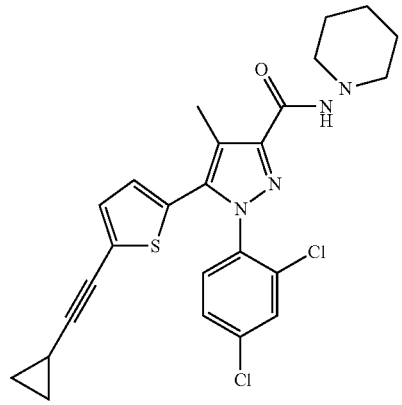

Compound 8

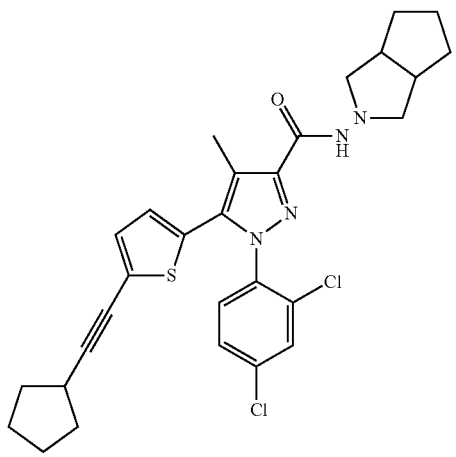

Compound 9

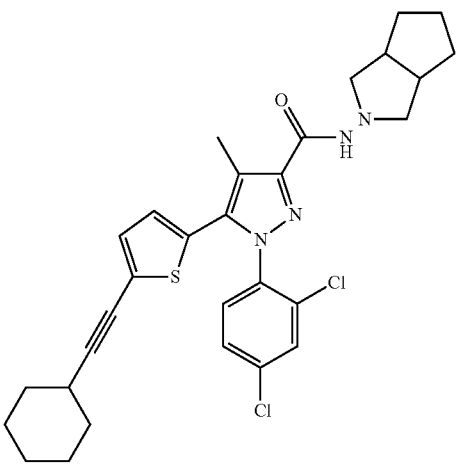

Compound 10

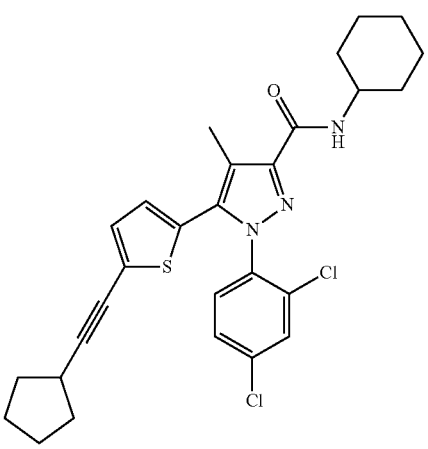

-continued
Compound 11
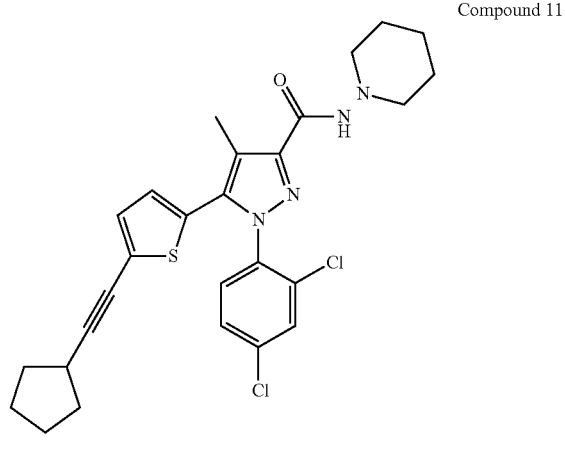
Compound 30
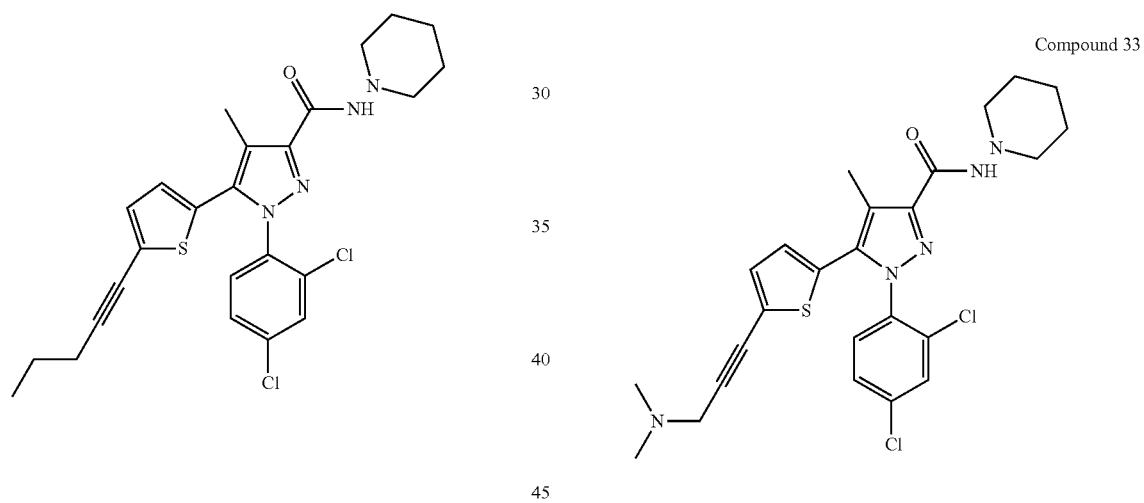
Compound 31
-continued
Compound 32
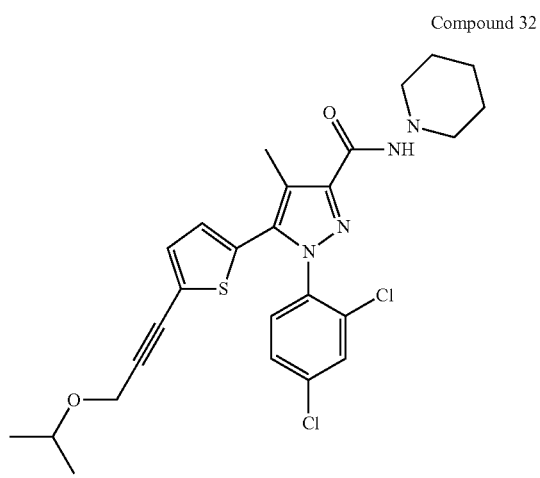
Compound 33
Compound 34
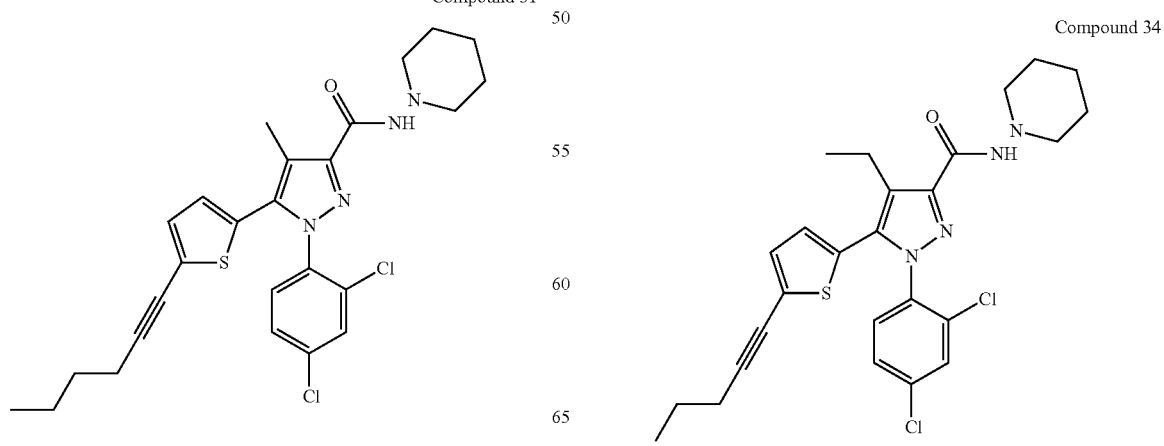

Compound 35

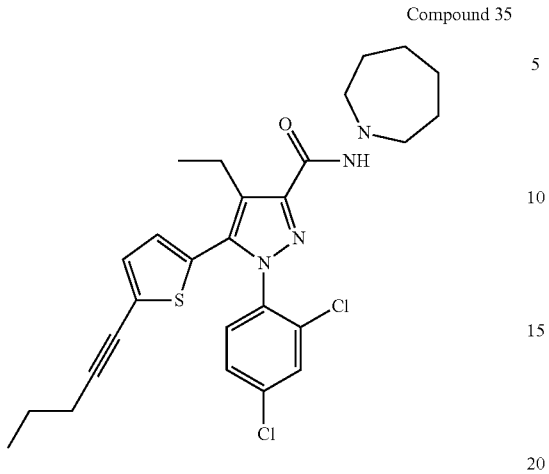

Compound 36

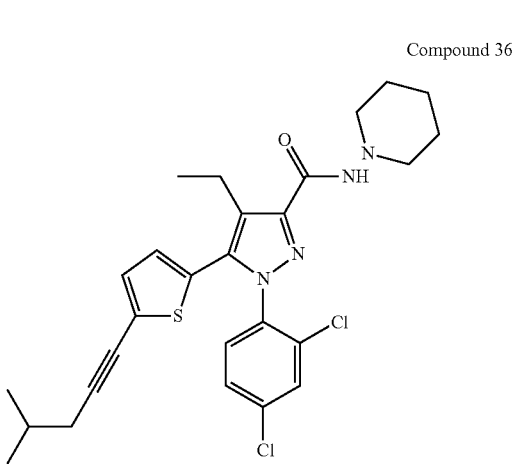

Compound 37

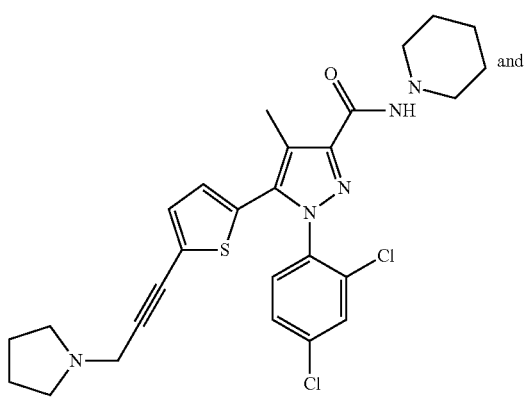

Compound 38

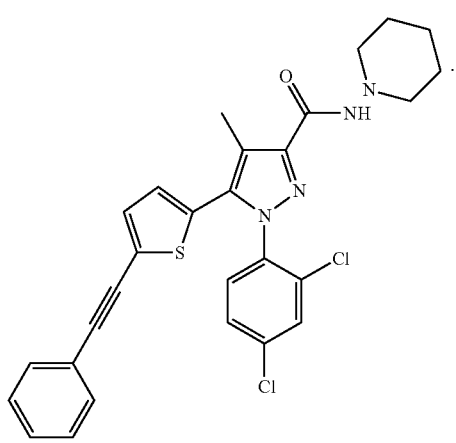

6. A compound of formula (I):

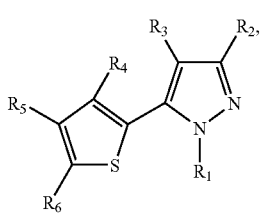
(I)

wherein
R$_1$ is aryl;
R$_2$ is H, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl, heteroaryl, halo, OR$_a$, COOR$_a$, OC(O)R$_a$, C(O)R$_a$, C(O)NR$_a$R$_b$, or NR$_a$R$_b$, in which each of R$_a$ and R$_b$, independently, is H, C$_1$-C$_{10}$ alkyl, C$_3$-C$_{20}$ cycloalkyl, C$_1$-C$_{20}$ heterocycloalkyl, aryl, or heteroaryl;
each of R$_3$, R$_4$, and R$_5$, independently, is H, halo, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, heterocycloalkyl, C$_1$-C$_{20}$ heterocycloalkenyl, aryl, or heteroaryl; or R$_5$, together with R$_6$ and the carbon atoms to which they are attached, is C$_3$-C$_{20}$ cycloalkenyl or C$_3$-C$_{20}$ heterocycloalkenyl; and
R$_6$ is C$_2$-C$_{10}$ alkenyl substituted with alkoxy, amino, cycloalkyl, heterocycloalkyl, aryl, or heteroaryl.

7. A compound of formula (I):

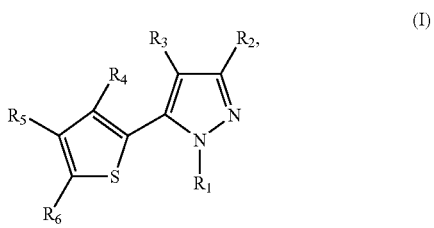
(I)

wherein
R₁ is aryl;
R₂ is C(O)Rₐ, in which Rₐ is piperidinyl or pyrrolidinyl, or C(O)NRₐR_b, in which each of Rₐ and R_b, independently, is H, cyclohexyl, piperidinyl, or octahydrocyclopentapyrrolyl;
each of R₃, R₄, and R₅, independently, is H, halo, $C_1$-$C_{10}$alkyl, $C_2$-$C_{10}$ alkenyl $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or R₅, together with R₆ and the carbon atoms to which they are attached, is $C_3$-$C_{20}$ cycloalkenyl or $C_3$-$C_{20}$ heterocycloalkenyl; and
R₆ is $C_2$-$C_{10}$ alkenyl or $C_2$-$C_{10}$ alkynyl; or R₆, together with R₅ and the carbon atoms to which they are attached, is $C_3$-$C_{20}$ cycloalkenyl or $C_3$-$C_{20}$ heterocycloalkenyl.

8. The compound of claim 4, wherein the compound is selected from compounds 1-6 shown below:

Compound 1

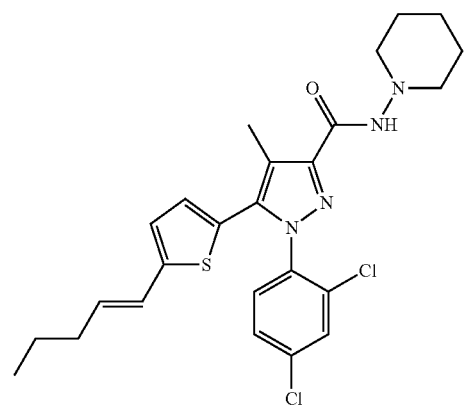

Compound 2

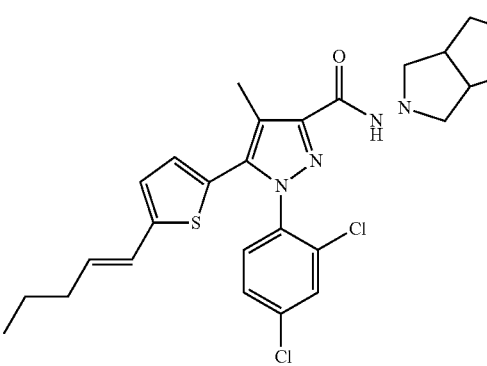

Compound 3

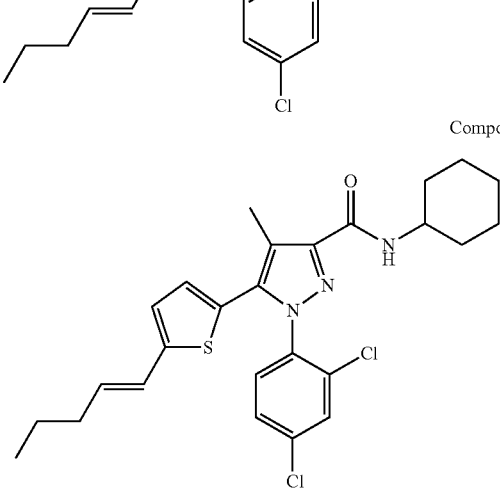

-continued

Compound 4

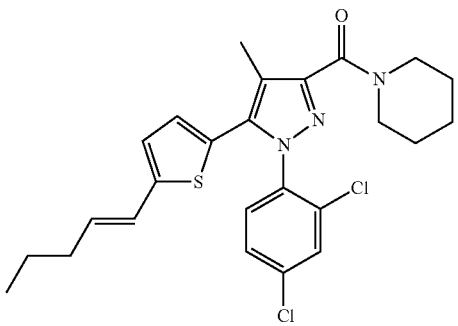

Compound 5

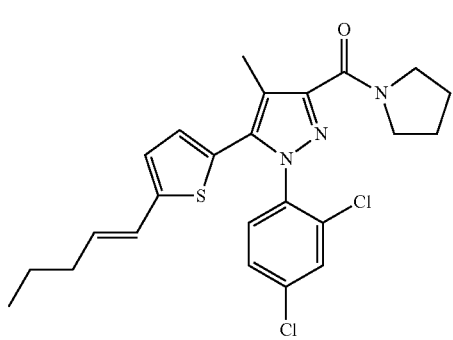

Compound 6

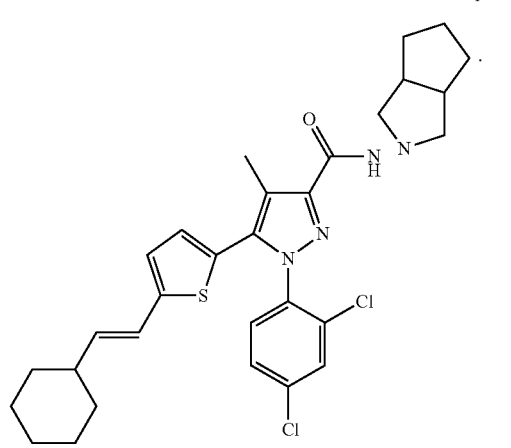

* * * * *